(12) United States Patent
McLauchlan et al.

(10) Patent No.: US 6,200,577 B1
(45) Date of Patent: Mar. 13, 2001

(54) ANTI-HERPESVIRAL AGENTS AND ASSAYS THEREFOR

(75) Inventors: John McLauchlan; Duncan James McGeoch; Ralph Graham Hope, all of Glasgow; Helen Winton McLaren Rixon, Strathblane, all of (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/230,421

(22) PCT Filed: Jul. 28, 1997

(86) PCT No.: PCT/GB97/02036

§ 371 Date: Jan. 25, 1999

§ 102(e) Date: Jan. 25, 1999

(87) PCT Pub. No.: WO99/04708

PCT Pub. Date: Feb. 5, 1998

(30) Foreign Application Priority Data

Jul. 26, 1996 (GB) .................................................. 9615726

(51) Int. Cl.[7] ........................ A61K 39/245; A61K 39/12; C12Q 1/70
(52) U.S. Cl. .................................... 424/229.1; 424/204.1; 424/231.1; 435/5; 435/975; 435/7.93; 530/300; 536/23.72
(58) Field of Search .............................. 435/5, 7.93, 7.94, 435/7.95, 975; 424/204.1, 229.1, 231.1; 530/300; 536/23.72

(56) References Cited

FOREIGN PATENT DOCUMENTS

0297924A2    1/1989  (EP) .
2259705A     3/1993  (GB) .

OTHER PUBLICATIONS

Elliott et al., "VP16 Interacts via Its Activation Domain with VP22, a Tegument Protein of Herpes Simplex Virus . . . ", Journal of Virology, vol. 69, No. 12, Dec. 1995, pp. 7932–7941.

Haigh et al., "Interference with the assembly of a virus–host transcription complex by peptide competition", Nature, vol. 344, Mar. 15, 1990, pp. 257–259.

*Primary Examiner*—Ali R. Salimi
(74) *Attorney, Agent, or Firm*—Ratner & Prestia

(57) ABSTRACT

There is described an antiviral agent capable of disrupting the association of two viral structural proteins required for maturation, replication and infection of herpesviruses. The agents are based upon VP22 and disrupt the normal association of that protein with VP16 and/or gB. Suitable agents are peptides having the amino acid sequences TPRVAG-FNKRVFCAAVGRLAAMHARMAAVQLW or ITTIRVTVCEGKNLLQRANE. The agents are suitable for combatting infection of herpesviruses and thus for the treatment of cod sores, genital herpes, chickenpox and shingles. An assay to test for agents able to disrupt VP22/V16 and/or VP22/gB association is also described.

13 Claims, 12 Drawing Sheets

| | | | | |
|---|---|---|---|---|
| MGSSHHHHHH | SSGLVPRGSH | MASTAPTRSK | TPAQGLARKL | 40 |
| HFSTAPPNPD | APWTPRVAGF | NKRVFCAAVG | RLAAMHARMA | 80 |
| AVQLWDMSRP | RTDEDLNELL | GITTIRVTVC | EGKNLLQRAN | 120 |
| ELVNPDVVQD | VPDPERKTPR | VTGG | | |

ANTI-HERPESVIRAL AGENTS AND ASSAYS THEREFOR

This application is the U.S. national phase application of PCT International Application No. PCT/GB97/02036 filed Jul. 28, 1997.

The present invention relates to an anti-viral agent effective against herpesviruses and to an assay for screening for other suitable anti-viral agents.

Herpesviruses are a large family of viruses which infect a wide range of organisms. The term "Herpesvirus" is used herein to refer to any virus of the Herpes family, including viruses in the a group (e.g. HSV, PrV), the β group (eg HCMV) and in the γ group (eg EBV). Seven herpesviruses are known to infect humans and there is evidence for an eighth human herpesvirus. The most highly characterised human herpesvirus is herpes simplex type 1 (HSV-1) which is associated with causing lesions around the mouth (cold sores). HSV-2, which is closely related to HSV-1, is a primary cause of genital infections. A common feature of herpesviruses is their ability to establish latent infections and recurrences of HSV-1 and HSV-2 infections are common among infected individuals. For a sizeable proportion of these individuals, recurrences are highly debilitating and impact upon quality of life. In other situations, HSV-1 and HSV-2 infection can be life-threatening. A third related virus, varicella zoster virus (VZV), is the causative agent of chickenpox in children and shingles in adults.

Herpesvirus virions consist of four morphologically distinct components, the core, capsid, tegument and envelope (reviewed in Rixon, 1993).

In virions made by HSV-1, the prototype a-herpesvirus, there are about 29 viral polypeptides in the tegument and envelope (15 to 18 polypeptides in the tegument and 11 glycoproteins in the envelope). Thus these two regions of virus particles account for more than 30% of the genes encoded by the virus genome. From studies on L-particles, which are virus-related particles that lack a nucleocapsid and are made by HSV-1, it has been demonstrated that the tegument and envelope can combine to assemble mature particles whose properties are indistinguishable from those of virions during the early events after infection (Szilágyi and Cunningham, 1991; McLauchlan et al., 1992; Rixon et al., 1992). The compositions of the tegument and envelope in virions and L-particles are also very similar (Szilágy! and Cunningham, 1991; McLauchlan and Rixon, 1992), hence, interaction with the capsid is not a primary determinant for incorporation into either of these sub-structures of virions. It follows that interactions between the tegument and envelope components play a critical role in particle assembly and maturation.

Three of the most abundant structural proteins are glycoprotein B (gB), VP16 and VP22. gB is located in the envelope while VP16 and VP22 are tegument proteins.

VP16 is the product of the UL48 gene and is 490 amino acid residues in length with an apparent molecular weight of 65 KDa on denaturing polyacrylamide gels. This protein plays an essential role in both activation of transcription of immediate early (IE) genes and the assembly of the progeny virions (Weinheimer et al., 1992; reviewed in O'Hare, 1993). Hence, deletion of this gene abrogates virus growth and, to date, it is the only tegument protein known to be essential for virus growth. Mutagenesis of the UL48 gene demonstrated that distinct regions of the VP16 protein are involved in transactivation and assembly (Ace et al., 1988). The sequences involved in transactivation can be separated into two domains. One domain, within the N-terminal portion of the protein, is specific for protein interactions with cellular transcription factors. Another domain is located within the C-terminal tail region of the polypeptide; this region is rich in acidic residues, however, apart from HSV-2, it is not conserved in homologues of VP16.

The function of the other major tegument protein, VP22, has not been well characterised. The protein is encoded by the UL49 gene (Elliott and Meredith, 1992) and the open reading frame (ORF) consists of 301 amino acid residues. On denaturing polyacrylamide gels, the protein has an apparent molecular weight of approximately 38 KDa. In infected cells, it is extensively modified post-translationally by phosphorylation, poly(ADP)ribosylation and nucleotidylylation (Blaho et al., 1994). Immunofluorescence studies have shown that, in infected cells, VP22 is located in the cytoplasm with high concentrations around the nuclear membrane (Elliott and Meredith, 1992). It also associates with the nuclear matrix and therefore may have DNA-binding ability (Knopf and Kaerner, 1980). Recent evidence has revealed that VP22 has the ability to exit and re-enter cells although the mechanism which mediates this property is unknown (Elliott and O'Hare, 1997). Within the tegument, VP22 is the most abundant structural protein and recent evidence has shown that its abundance in the tegument can be further enhanced by altering the amount of VP22 produced during infection (Leslie et al., 1996). we have evidence that mutations within this protein significantly reduce virus growth (J. McLaughlan and Y. Sun, unpublished data). In a related bovine herpesvirus, the removal of the gene that encodes the protein homologous to VP22 severely impairs virus growth (Liang et al., 1995).

gB is the most abundant of the envelope components. It is encoded by gene UL27 and is the most highly conserved gene among those encoding herpesvirus glycoproteins. Along with three other glycoproteins (gD, gH and gL), it is essential for virus replication in tissue culture and is required for virus penetration and cell to cell spread. The unprocessed polypeptide consists of 904 residues and, on denaturing polyacrylamide gels, the mature species has an apparent molecular weight of about 120 KDa. The encoded polypeptide can be separated into four domains: a cleavable signal sequence of 30 residues, an ectodomain (external domain) of 697 residues, a hydrophobic transmembrane domain of 68 amino acids and an extensive endodomain (cytoplasmic region) of 109 amino acids (Cai et al., 1988). The cytoplasmic domain is reported to have a role in cell-cell fusion and this is supported by the mapping of syn mutations to this region (Bond et al., 1982; Gage et al., 1993). The biologically active form of gB is an oligomer. Two discontinuous sites for oligomer formation have been characterised, a non-essential region in the N-terminal portion of the mature polypeptide and an essential site proximal to the membrane-spanning domain (Highlander et al., 1991; La Querre et al., 1996). Defective forms of gB, which retain the ability to form hetero-oligomers, inhibit complementation of gB null mutants by the wild-type gB molecule and thus exhibit negative transdominance (Cai et al., 1988). Among the mutants which display this property are C-terminally truncated forms which retain the transmembrane domain and the regions required for oligomerisation but lack the cytoplasmic tail.

Following treatment of virus particles with a cross-linking reagent, four structured proteins, which were not present on the virus envelope, were co-precipitated with gB using a gB-specific polyclonal antiserum (Zhu and Courtney, 1994); this suggested that, in the virus particle, gB is in close proximity to these proteins. One of these proteins was immunologically characterised to be VP16, two were tentatively identified as VP11/12 (encoded by gene UL46) and VP13/14 (encoded by gene UL47) and the fourth was not classified but did have the same apparent molecular weight as VP22. From the topography of gB, it is reasonable to speculate that the cytoplasmic domain of the protein may interact with tegument proteins underlying the envelope. Blocking any interaction of the C-terminal domain of gB with tegument proteins may inhibit incorporation of the protein into virions, thus generating virus with either no or reduced infectivity. This could be achieved through binding of a peptide or a peptide derivative to the intracellular domain of wild type gB.

Recent studies have shown that VP16 and VP22 also interact (Elliott et al., 1995). This interaction is detected in infected cells by immunoprecipitation of the complex by a VP16-specific antibody. Interestingly, co-expression of VP16 and VP22 in transfected cells, in the absence of other HSV proteins, leads to relocalisation of both proteins to novel spherical structures termed tegument bodies. Experiments with baculovirus recombinants expressing these proteins have revealed that indistinguishable structures are produced in insect cells (J. McLauchlan and F. J. Rixon, unpublished data). Thus, tegument bodies are likely to result from the interaction between VP16 and VP22.

In addition to the formation of virus particles, tegument proteins also have a role during the initial stages of infection. Hence, inhibiting the function of tegument proteins has the potential for disabling the infectious process both during virus assembly and at some other stage of infection.

The action of VP16 requires intimate involvement with other proteins and thus the complex formed with VP22 could be crucial to either or both of the functions assigned to VP16. The region of VP16 which is involved in this interaction is at the C-terminus of the protein and this is the domain that has a role in activating the IE viral genes.

gB, VP16 and VP22 have been described previously in the literature. McGeoch et al. (1988) disclosed the whole nucleotide sequence and the predicted amino acid sequences of HSV-1 strain 17 including genes UL27, UL48 and UL49 which encode gB, VP16 and VP22 respectively. All 3 genes are leftward orientated on the prototype orientation of the virus genome.

The nucleotide sequence of HSV-1 strain 17, containing the full coding sequences of gB, VP16 and VP22, is available from publically accessible databases under Accession Number X14112.

The construction of clones of gB, VP16 and VP22 nucleotide coding sequences is well within the scope of abilities of the skilled man, and such coding sequences could be generated de-novo by DNA synthesis or derived from publically accessible clones by established PCR techniques.

The present example describes interactions which occur between gB and VP22 and between VP16 and VP22. Using truncated forms of these proteins which have been expressed in bacteria, the regions involved in the interactions have been located to the C-terminal 107 residues of gB (the endodomain of the protein), a 109 residue region of VP22 encoded by nucleotides 105590 to 105919 of HSV-1 (hereafter termed the C-proximal region of VP22) and the N-terminal 412 residues of VP16. Association between VP22 and gB had not been established previously.

As is further described in the examples, synthetic peptides (A to J; Table 1) have been tested for their ability to interfere with the association between VP22 and VP16 or between VP22 and gB and suitable assays have been developed. We have found that peptides D and E prevent association of VP22 and VP16 and also prevent association of VP22 and gB. A further peptide, peptide H, is capable of binding to VP16, but whilst it does not prevent interaction with VP22, peptide H does inhibit VP22/gB association. One explanation of this observation is the presence of two sites on VP22 where VP16 and gB may interact. A combination of antiviral agents able to disrupt association at these two putative sites could be advantageous.

According to the present invention there is provided an antiviral agent capable of combatting maturation and/or replication of a herpesvirus by disrupting association of VP22 with VP16 and/or gB.

A suitable agent would be the highly conserved oligopeptide TPRVAGFNKRVFCAAVGRLAAMHARMAAVQLw (encoded from nucleotides 105728 to 105823 on the HSV-1 genome corresponding to the gene UL49), or a portion or functional equivalent thereof. In particular, the oligopeptides TPRVAGFNKRVFCAAVGRLA (peptide D) and CAAVGRLAAMHARMAAVQLW (peptide E) have been found to prevent association of VP22 with VP16 and/or VP22 with gB.

A second suitable agent would be the oligopeptide ITTIRVTVCEGKNLLQRANE (encoded from nucleotides 105621 to 105680 on the HSV-1 genome corresponding to the gene UL49), or a portion or functional equivalent thereof. This oligopeptide (peptide H) has been found to bind to VP16 and to prevent association of VP22 with gB.

The portion of VP22 identified above has been predicted to comprise a helix. It is possible that the secondary structure is of equal or greater importance for the binding to VP16 and gB than the precise nucleotide or amino acid sequence. The present invention thus encompasses variants or mutations of the above VP22 domain which have no substantial effect on the binding function.

The anti-viral agent may be a peptide (for example, the peptides indicated above) or a peptidomimetic compound which would be resistant to enzymic breakdown by peptidases. Peptidomimetic compounds of peptides A–H (especially peptides D, E and H) form part of the invention.

The antiviral agent can preferably prevent either assembly of infectious virus particles or the activation of virus genes or the infectivity of progeny virus. The most widely used conventional anti-HSV compound, and much of the current development of other therapies, relies on the interruption of DNA replication to block virus growth. Compounds which are active at other stages of the virus growth cycle have the potential to act in concert with, or independently from, conventional therapies. In addition, since homologues of the genes encoding gB, VP16 and VP22 are present in other a-herpesviruses, anti-HSV compounds could be effective against or further developed for treatment of other conditions such as chickenpox or shingles caused by VZV.

The anti-viral agent may be a peptide, either synthetic or derived wholly or partially from a natural protein. Suitable anti-viral compounds include peptides having an amino acid sequence derived from VP22 (especially the C-proximal region of VP22) or a functional equivalent of such a peptide. Peptidomimetic compounds therefor may be suitable anti-viral agents. The agent preferably binds to at least a portion of either gB or the VP16 C-terminus.

In a further aspect, the present invention provides an assay to determine the ability of a test substance to interfere with the association of VP16 and VP22 or with the association of gB and VP22. The assay comprises the following steps:

i) providing a first viral component;
ii) exposing said first viral component to a test substance followed by a second viral component, or exposing said first viral component to a second viral component followed by a test substance;
iii) washing to remove any second viral component and/or test substance not associated with the first viral component; and
iv) detecting the presence, and optionally determining the amount, of second viral compound associated with said first viral component.

The first or second viral components may be localised on a surface, such as a blotting membrane, or an assay plate for ELISA etc. Preferably the first viral component is immobilised in such a manner, although the invention contemplates the possibility of the assay being carried out in solution.

The first viral component may be gB, VP16 or VP22. Where the first viral component is either gB or VP16, the second viral component will be VP22. Where the first viral component is VP22, the second viral component will be either VP16 or gB.

Detection of the presence and/or amount of second viral component associated with the first viral component may be conducted by any convenient means. Generally detection may be via an antibody (preferably monoclonal), the presence of which can be established by exposure to a second labelled antibody (again preferably monoclonal) in a typical ELISA-style assay, although direct labelling of the first antibody (or even one of the viral components) is possible.

The invention also provides a method of combatting viral maturation and/or replication of a herpesvirus, the method comprising providing an agent capable of interfering with the interaction of gB and/or VP16 with VP22.

The invention also provides the use of an agent capable of interfering with VP16/VP22 association or with gB/VP22 association for combatting herpesvirus infection, replication or maturation, and for the manufacture of a medicament for combatting herpesvirus infection, replication or maturation.

(B) The predicted sequence of VP22trunc. The regions of the polypeptide that are not derived from VP22 but which contain the histidine and epitope tag motifs are underlined. The sequence is given in SEQ ID No 3.

Figure 2:
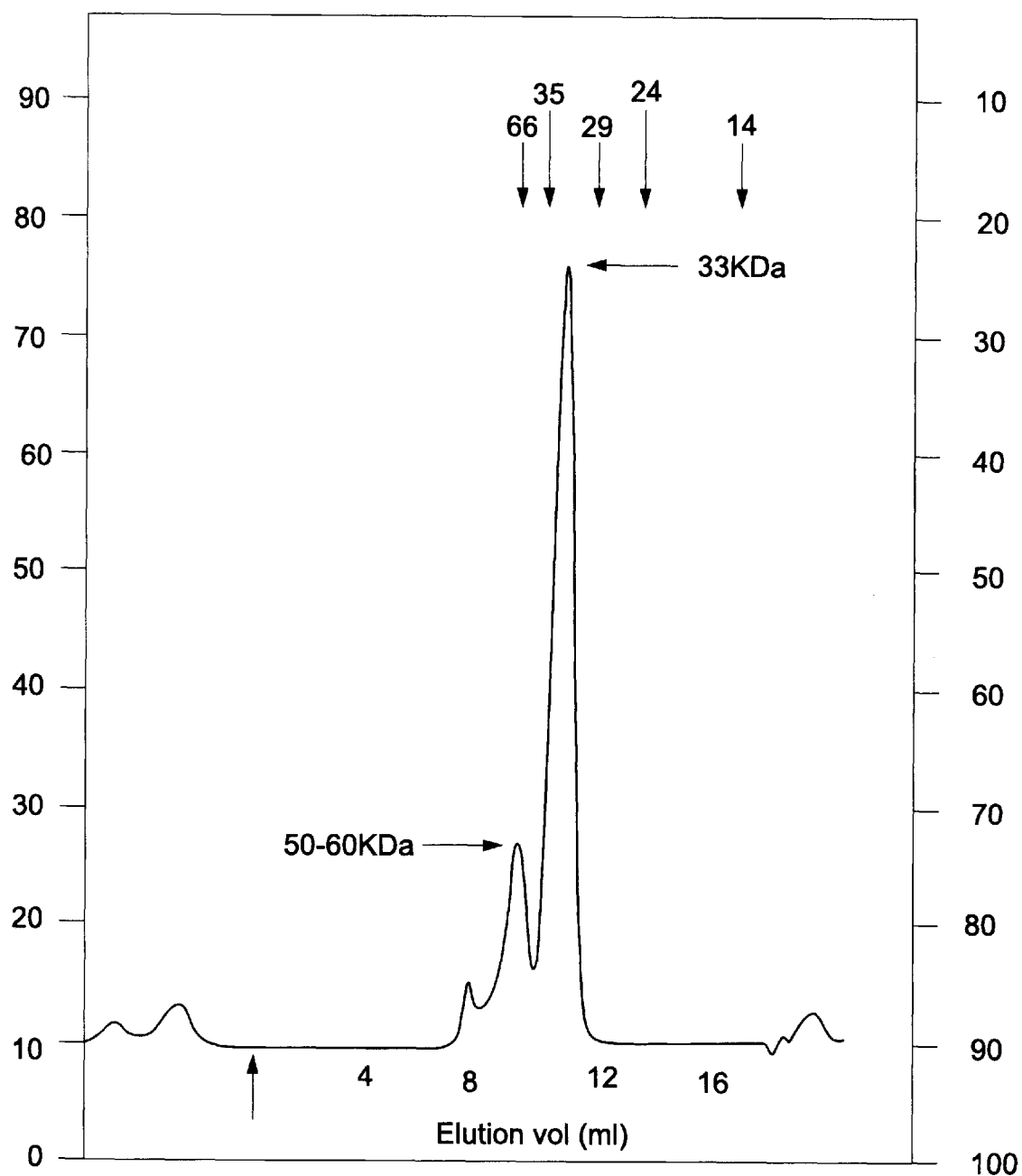

FIG. 2 Molecular weight determination of VP22trunc by FPLC. 200pl of VP22trunc at a concentration of 0.5 mg/ml was applied to a Superdex 75 10/30 column. The column was run at a flow rate of lml/min. The point at which the sample was applied to the column is arrowed. Proteins were detected by absorption at 280 nm. The molecular weight of VP22 was determined by comparison with the relative mobilities of marker proteins of known sizes. These were: lysozyme (14 KDa), trypsin (24 KDa), carbonic anhydrase (29 KDa), pepsin (35 KDa) and BSA (66 KDa).

Figure 3:
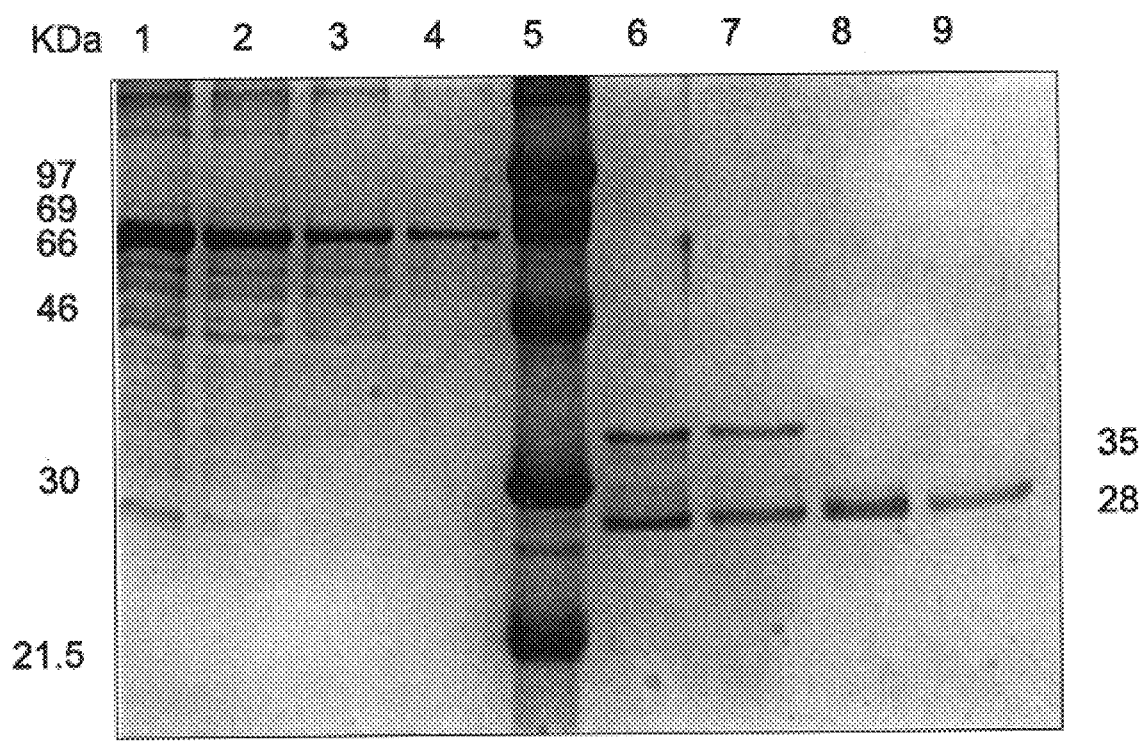

FIG. 3 Quantitative analysis of purified GST-gB fusion protein. Proteins were separated on a 12% polyacrylamide gel and then stained with Coomassie Brilliant blue. Samples were as follows: lane 1, 10 μg of BSA; lane 2, 5 μg of BSA; lane 3, 2.5 μg of BSA; lane 4, 1.25 μg of BSA; lane 5, molecular weight markers; lane 6, 10 μl of purified GST-gB; lane 7, 5 μl of purified GST-gB; lane 8, 10 μl of purified GST; lane 9, 5 μl of purified GST. The sizes of polypeptides (in KDa) are indicated.

Figure 4:
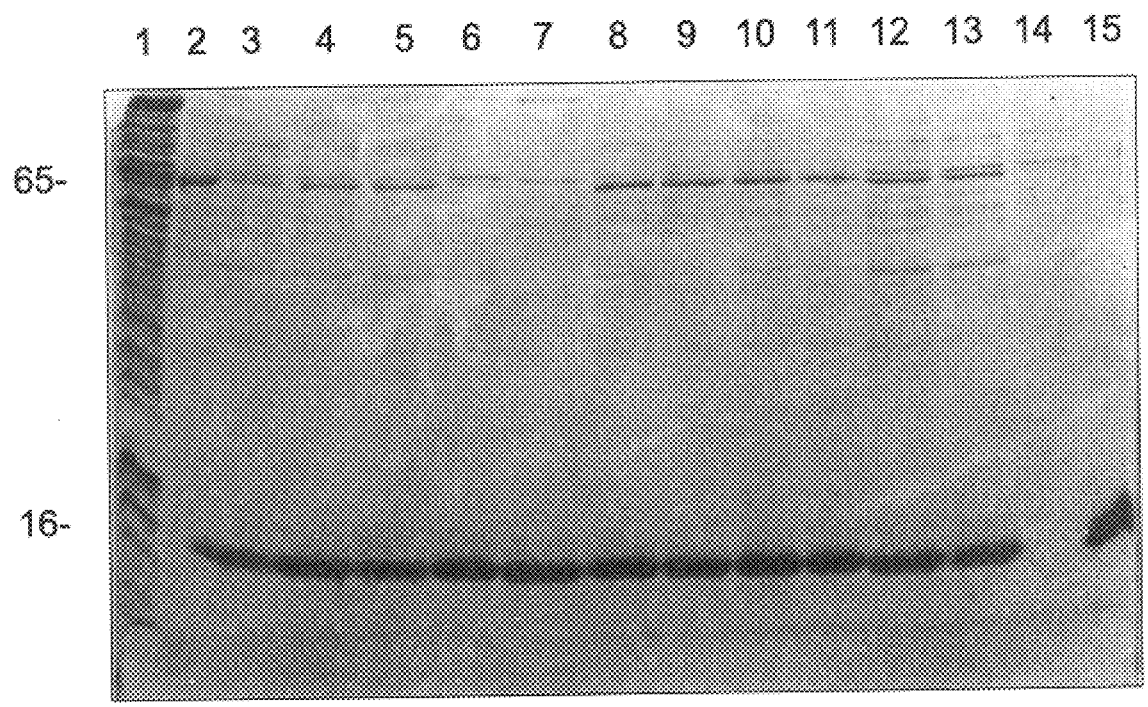

FIG. 4 Co-elution of VP16 with VP22trunc from Ni-NTA resin. Partially purified extract containing VP16 was incubated in the absence of (lane 14) or presence of 10 gg of VP22trunc (lanes 3 to 13). In lanes 3 to 12, an equal volume of the individual peptides at 2 mg/ml was added to the extract prior to VP22trunc. Peptides added to each reaction were as follows: lane 3, peptide A; lane 4, peptide B; lane 5, peptide C; lane 6, peptide D; lane 7, peptide E; lane 8, peptide F; lane 9, peptide G; lane 10, peptide H; lane 11, peptide I; lane 12, peptide J; lane 13, no peptide. Lanes 3 to 14 show the polypeptides eluted from Ni-NTA resin. Other samples were as follows: lane 1, partially purified VP16 extract, lane 2, purified VP16; lane 15, purified VP22trunc. Samples were electrophoresed on a 12% polyacrylamide gel and the apparent molecular weights of VP16 (65 KDa) and VP22trunc (16 KDa) are shown.

FIG. 5 Far Western blot analysis of VP16 binding to VP22.

(A) Binding of VP116 to immobilised VP22trunc. Purified VP22trunc was added to partially purified VP16 extract and the sample was run on a 12% polyacrylamide gel. Proteins were then transferred to nitrocellulose membrane and the blot was cut into strips, with each strip containing at least 2 μg of VP22trunc. Strips were incubated with no protein (lane 1), 2 μg of purified VP16 (lane 2) or 2 μg of purified VP16trunc (lane 3); bound VP16 was detected by antibody LP1 (1:1000 dilution). In lane 4, the membrane was incubated with the 9220 antibody (1:1000). The apparent molecular weights of VP16 (65 KDa) and trimer (48 KDa), dimer (32 KDa) and monomer (16 KDa) forms of VP22trunc are shown.

(B) Binding of VP16 to truncated forms of VP22 expressed in bacteria. Samples were electrophoresed on a 12% polyacrylamide gel and then proteins were transferred to nitro-cellulose membrane. Samples were as follows: lane 1, uninduced extract of VP22/172-259; lanes 2 and 6 VP22/159-301; lane 3, VP22/159-301mut; lanes 4 and 7, VP22trunc; lanes 5 and 9 VP22/172-259; lane 8, VP22/159-259. Lanes 2 to 5 contain crude extracts in which expression has been induced. Lanes 6 to 9 contain proteins purified on Ni-NTA resin. The blot was incubated with VP16 (2 mg/ml), followed by LP1 antibody (1:1000 dilution). The apparent molecular weights (in KDa) of the truncated forms of VP22trunc are shown.

Figure 6:
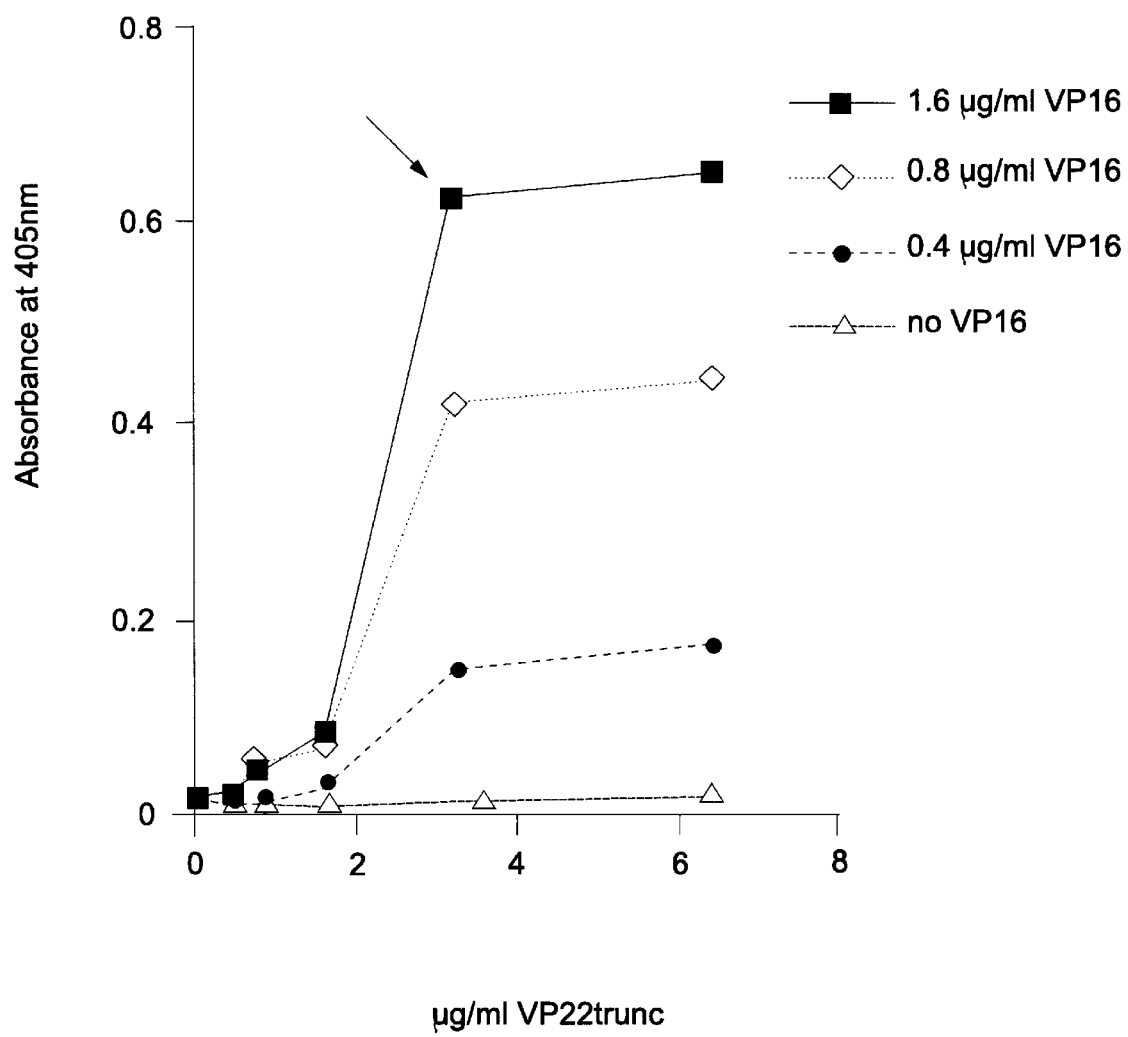

FIG. 6 ELISA of VP16 binding to VP22trunc. Microtitre wells were coated with a range of quantities of VP22trunc in duplicate (0 ng, 20 ng, 40 ng, 80 ng, 160 ng and 320 ng). After blocking, VP16 was added at various concentrations and then detected with LPI antibody at a 1:1000 dilution. The legend for the concentrations of VP16 added is shown to the right of the graph. Data points were determined by calculating the average value of duplicates. The data point obtained with the concentrations of VP22 and VP16 which were used in subsequent ELISA tests is arrowed.

Figure 7:
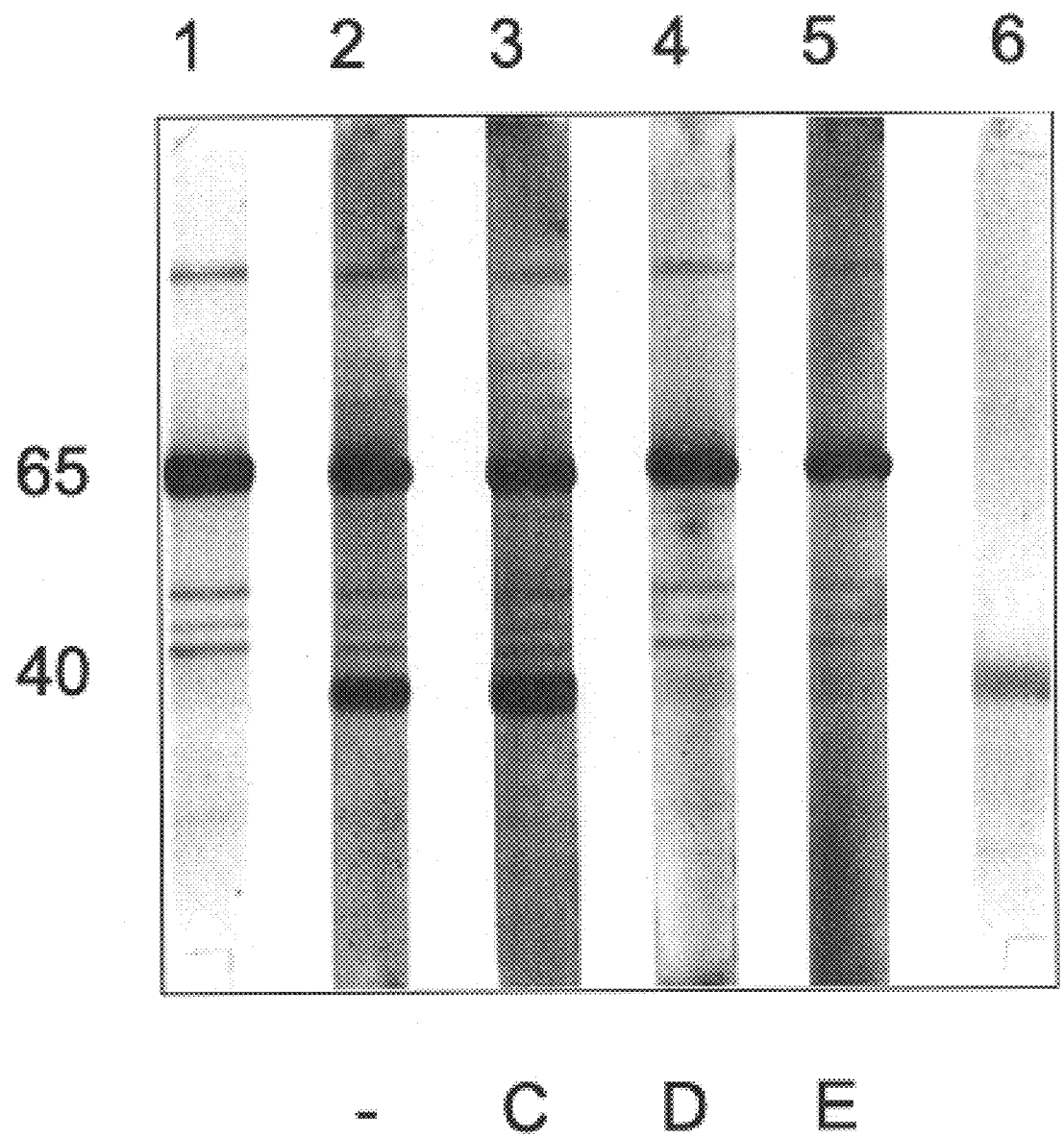

FIG. 7 Far Western analysis of the ability of peptides to block the interaction between VP16 and immobilised VP22trunc. Purified VP22trunc was added to partially purified extract of VP16 and the sample run on a 12% polyacrylamide gel. Proteins were then transferred to nitrocellulose membrane and the blot was cut into strips, with each strip containing approximately 1 g of VP22trunc. In (A), strips were pre-incubated with 1 mg of each of the following peptides: lane 2, no peptide, lane 3, peptide C; lane 4, peptide D; lane 5, peptide E; lane 6, peptide F; lane 7, peptides D and E; lane 8, peptides C and F. In (B) strips were pre-incubated with 1 mg of each of the following peptides: lane 2, no peptide, lane 3, peptide C; lane 4, purified peptide D; lane 5, purified peptide E; lane 6, peptide F. 24 g of pure VP16 was then added to strips 2 to 8 in (A) and strips 2 to 6 in (B), followed by incubation with LP1 antibody (1:1000 dilution). As a control, portions of the blot were incubated with LP1 or the 9220 antibody at a dilution of 1:1000 (lane 1 for LP1 in A and B; lane 9 in A and lane 7 in B for 9220). The apparent molecular weights of VP16 (65 KDa) and the dimer (32 KDa) and monomer (16 KDa) forms of VP22trunc are shown.

Figure 8:
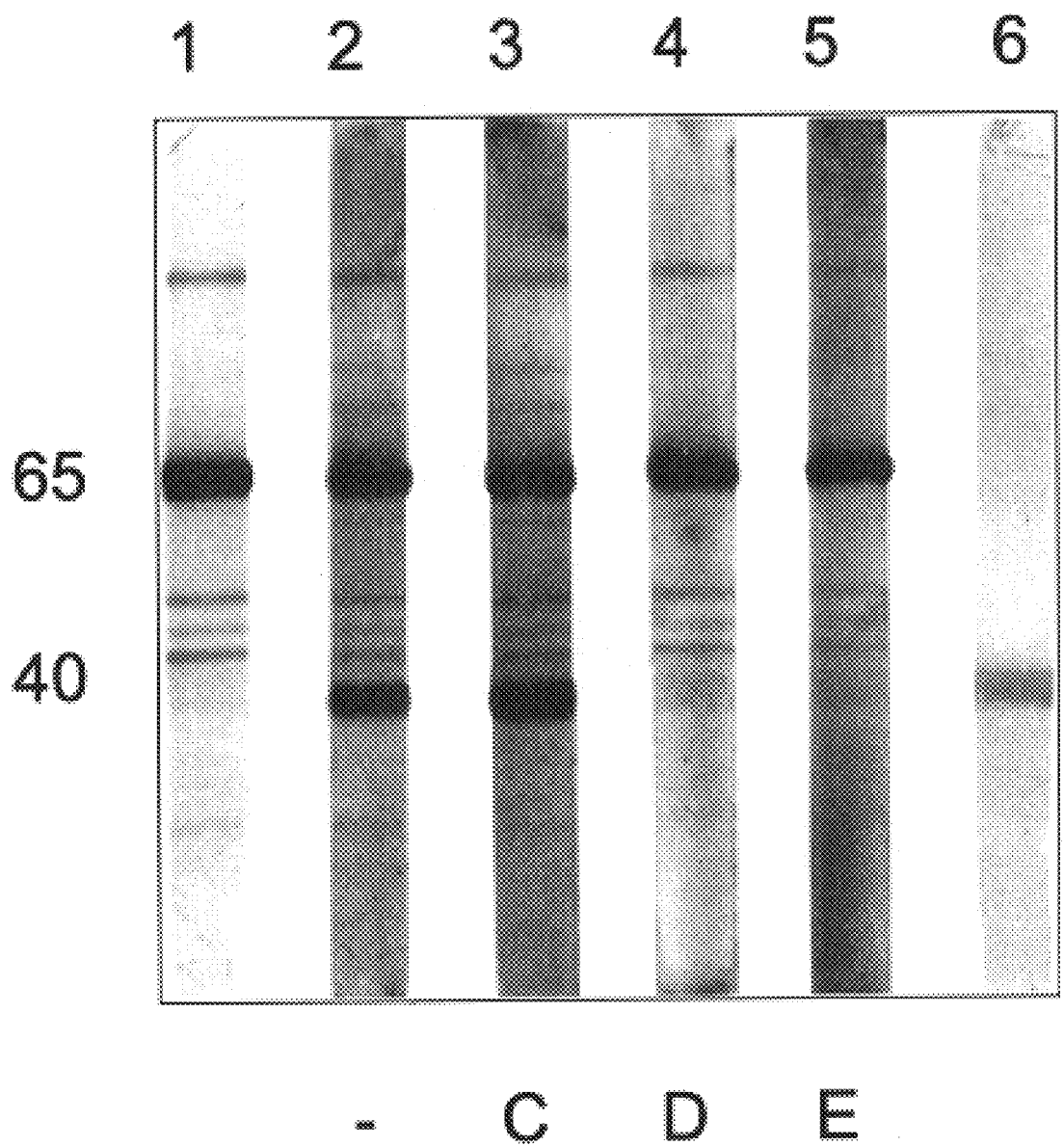

FIG. 8 Blocking of the interaction between VP16 and full length VP22 by pure peptides D and E. A vUL49ep L-particle extract was run on a 10% polyacrylamide gel and the proteins transferred to a nitrocellulose membrane. The blot was cut into strips, with each strip containing the equivalent of approximately $3 \times 10^9$ L-particles. Strips were pre-incubated with 1 mg of each of the following peptides: lane 2, no peptide; lane 3, peptide C; lane 4, peptide D; lane 5, peptide E. 2 µg of pure VP16 was then added to each incubation and bound VP16 was detected by LP1 antibody. Two strips were incubated with either LP1 (lane 1) or 9220 antibody (lane 6), each at a dilution of 1:1000. The apparent molecular weights of VP16 (65 KDa) and tagged VP22 (40 KDa) are shown.

Figure 9:
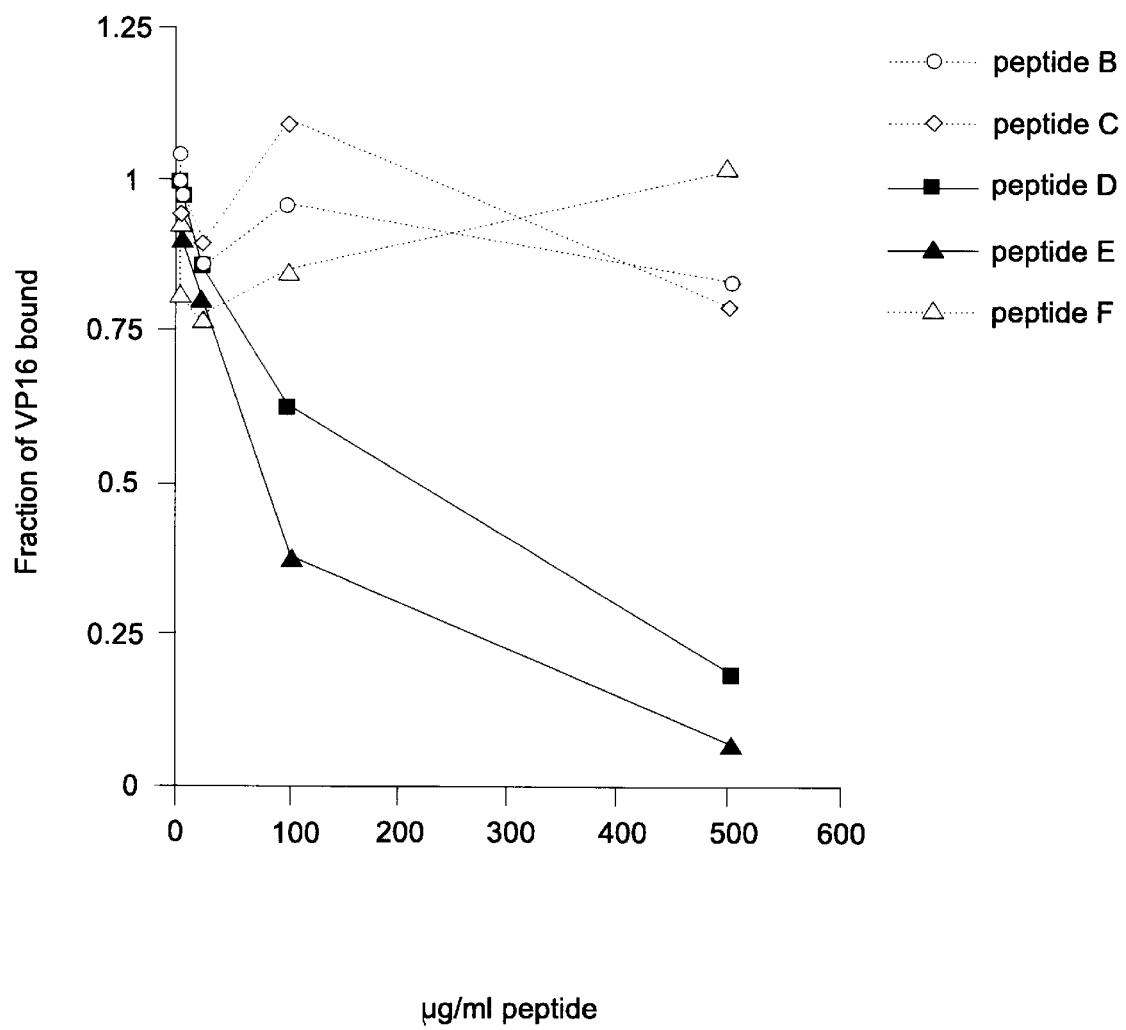

FIG. 9 Inhibitory effect of peptides D and E on the VP22trunc-VP16 interaction in ELISAs. Microtitre plates were coated with 160 ng of VP22trunc and blocked with PBS/10% NCS. Before addition to the wells, five-fold dilutions of the peptides, ranging from 500 µg/ml to 1 g/ml, were incubated with VP16 (1.6 µg/ml). Bound VP16 was detected with LP1 at a dilution of 1:1000. The legend for the peptides added is shown to the right of the graph. Values are shown relative to those obtained in the absence of the peptide.

Figure 10:
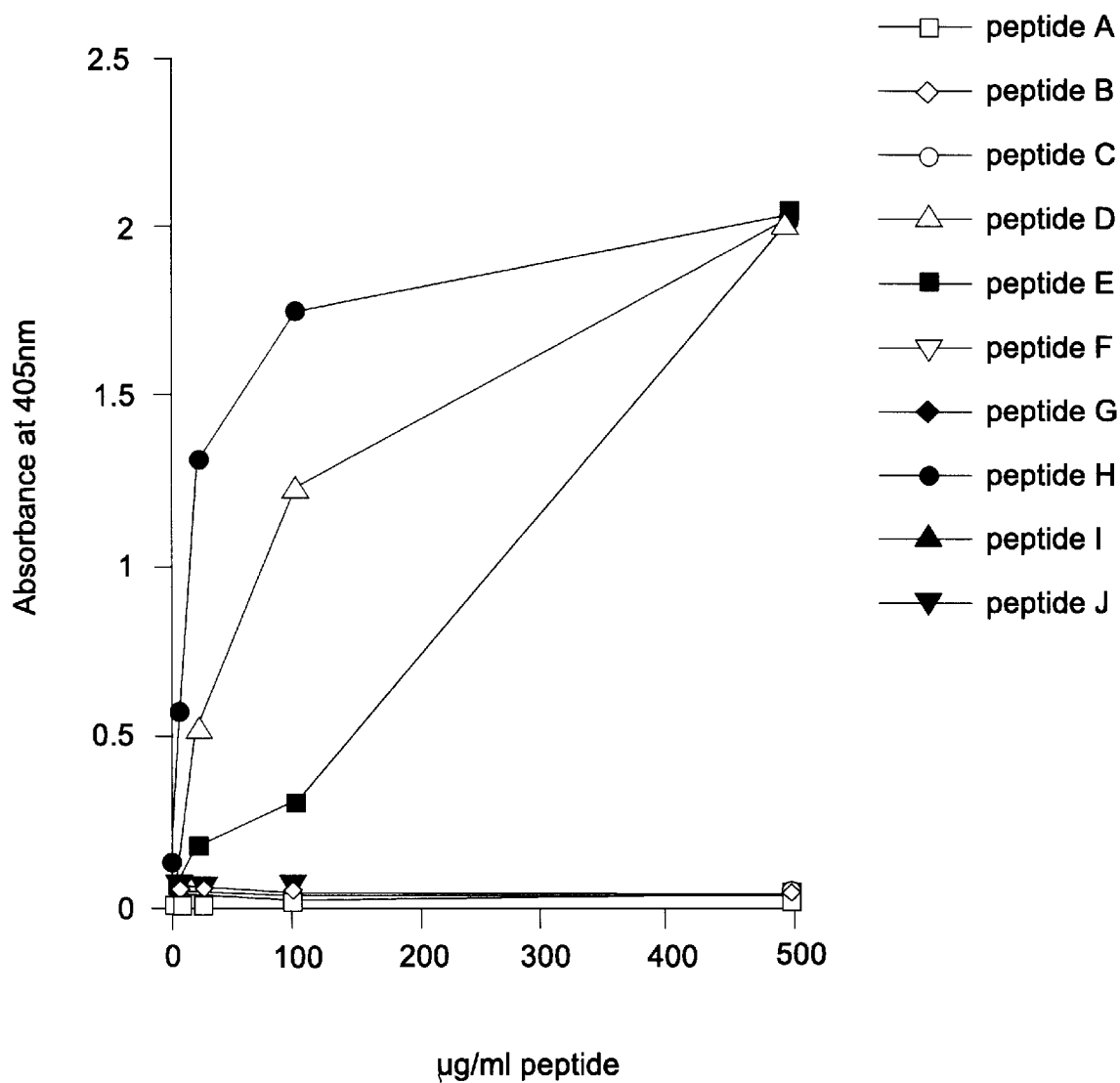

FIG. 10 Binding of VP16 to peptides. Microtitre plates were coated with 5-fold dilutions of peptides ranging from 500 µg/ml to 1 µg/ml and blocked with PBS/10% NCS. VP16 was then added to a final concentration of 1.6 µg/ml and detected with LP1. The legend for the peptides added is shown to the right of the graph.

Figure 11:
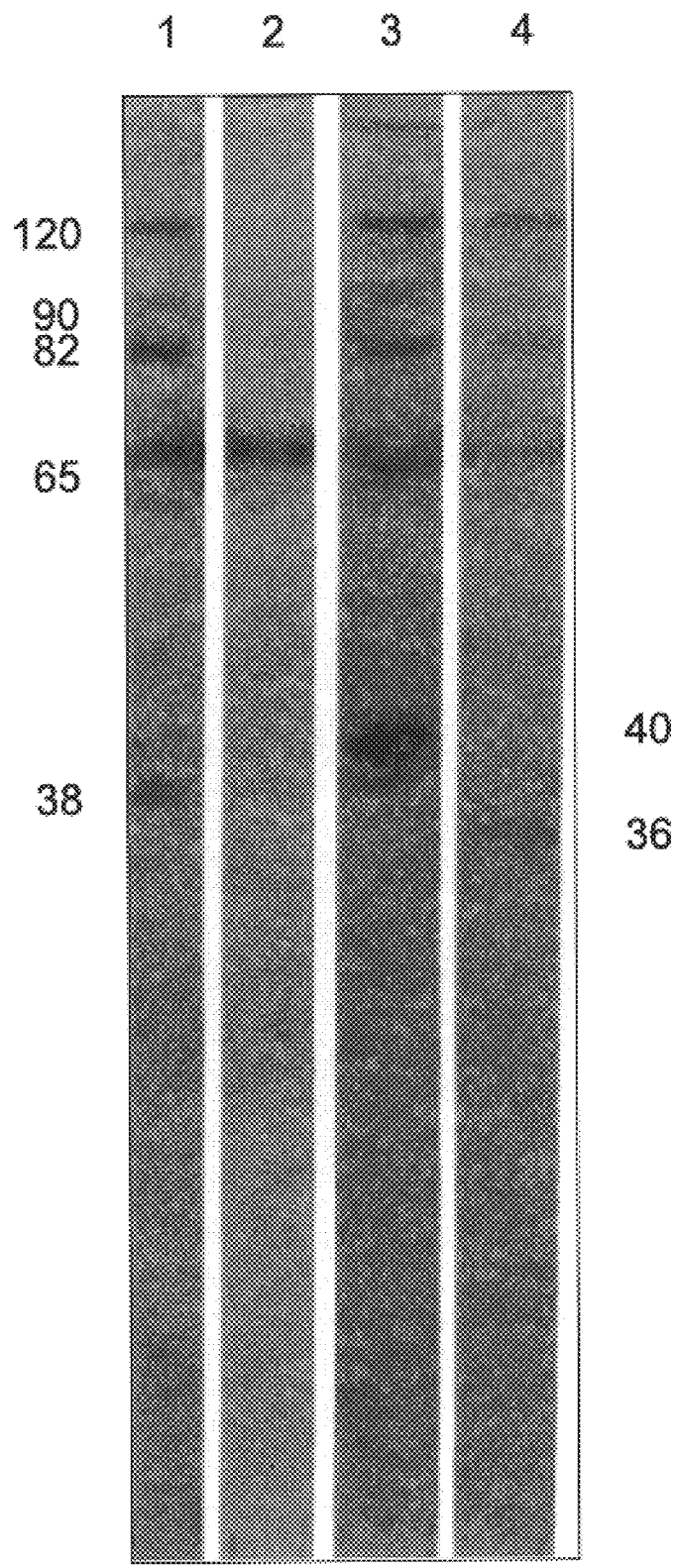

FIG. 11 Far Western blot analysis of GST-gB binding to purified HSV-1 virions and L-particles. Virus particles (approximately $3 \times 10^9$ particles per sample) were electrophoresed on a 15% polyacrylamide gel and blotted on to Problott membrane. Portions of the membrane were incubated with either purified GST-gB (lanes 1, 3 and 4) or GST (lane 2) at a final concentration of 1.2 µg/ml. Bound protein was detected with anti-GST antibody. Samples were as follows: lanes 1 and 2, HSV-1 strain F virions; lane 3, vUL49ep L-particles; lane 4, vUL49Δ268-301 L-particles. The apparent molecular weights of proteins are indicated.

Figure 12:
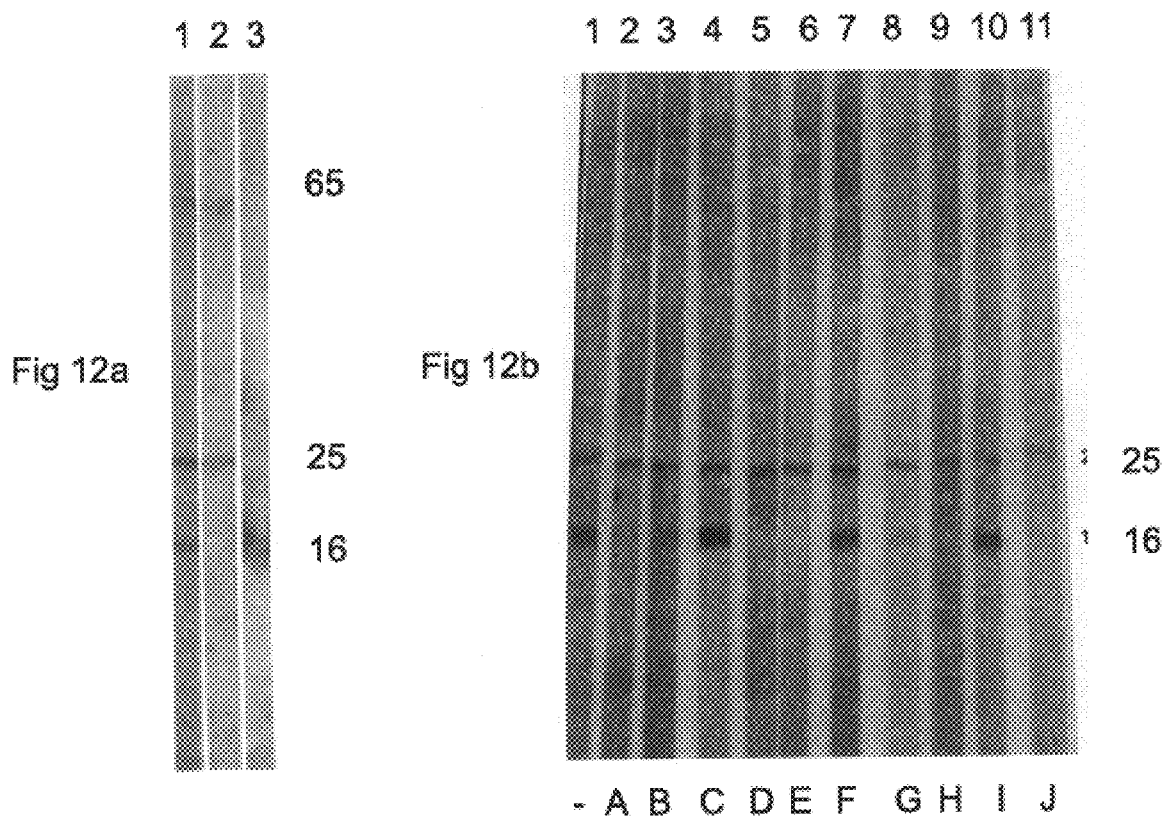

FIG. 12 Far Western blot analysis of the interaction between GST-gB and VP22trunc. Purified VP22trunc was electrophoresed on a 15% polyacrylamide gel. Proteins were transferred to PVDF membrane and the blot was cut into strips, with each strip containing approximately 1–2 µg of VP22trunc.

(A) Binding of GST-gB to VP22trunc. Strips were incubated with either purified GST-gB (lane 1) or GST (lane 2) at a final concentration of 1.2 µg/ml and the bound protein was detected with anti-GST antibody. In lane 3, the membrane was incubated with 9220 antibody.

(B) Inhibition of binding of GST-gB (final concentration 1.2 µg/ml)and each of the following peptides at a final concentration of 250 µg/ml: lane 1, no peptide; lane 2, peptide A; lane 3, peptide B; lane 4, peptide C; lane 5, peptide D; lane 6, peptide E; lane 7, peptide F; lane 8, peptide G; lane 9, peptide H; lane 10, peptide I; lane 11, peptide J. Bound GST-gB was detected with anti-GST antibody.

The apparent molecular weights of VP22trunc (16 KDa) and non-specific species detected by GST-gB (65 KDa and 25 KDa) are shown.

| SEQ ID No 1 | Nucleotide and predicted amino acid sequence of the UL49 gene which encodes VP22 (McGeoch et al., 1988) |
|---|---|
| SEQ ID No 2 | Predicted amino acid sequence from SEQ ID No 1 |
| SEQ ID No 3 | Predicted sequence of Vp22trunc |
| SEQ ID No 4 | Peptide A (see Table 1) |
| SEQ ID No 5 | Peptide B (see Table 1) |
| SEQ ID No 6 | Peptide C (see Table 1) |
| SEQ ID No 7 | Peptide D (see Table 1) |
| SEQ ID No 8 | Peptide E (see Table 1) |
| SEQ ID No 9 | Peptide F (see Table 1) |
| SEQ ID No 10 | Peptide G (see Table 1) |
| SEQ ID No 11 | Peptide H (see Table 1) |
| SEQ ID No 12 | Peptide I (see Table 1) |
| SEQ ID No 13 | Peptide J (see Table 1) |

The present invention will now be described by way of 24 example with reference to the accompanying figures and to the following examples.

EXAMPLES

Methods

Maintenance of Cells and Growth of Viruses.

BHK C13 cells were maintained in Glasgow modified Eagle's medium supplemented with 10% tryptose phosphate broth and 10% newborn calf serum.

The virus strains used in this study were HSV-1 wild-type strains 17 (Brown et al., 1973) and strain F (Ejercito et al., 1968), vUL49ep (Leslie et al., 1996) and vUL49Δ268-301 (Leslie, 1996). For growth of virus, BHK cells were infected at a multiplicity of infection (m.o.i.) of 1/300 PFU per cell. Following infection at 31° C. for 4 days, the virus was harvested and virions and L-particles were purified on 5–15% Ficoll gradients as described by Szilagyi and Cunningham (1991).

Plasmids.

(i) VP22 constructs. The parent plasmid for the constructs which expressed the truncated forms of VP22 was pET28a (Novagen). This plasmid contains T7 RNA polymerase promoter and terminator sequences. These transcription control regions flank sequences which encode an ATG initiation codon followed by a translated region that encodes a stretch of 6 histidine residues. Downstream from the sequences are unique restriction enzyme sites (NdeI and NheI) which are used for cloning purposes. pET28a also contains the LacI gene to repress expression under non-inducing conditions and the kanamycin resistance gene for antibiotic resistance.

Plasmid pYS360 (FIG. 1A) was constructed by inserting a 380 bp HincII DNA fragment from another plasmid pUL49Δ268-301 (Leslie, 1996) into the NheI site of pET28a. This fragment consists of nucleotides 521 to 845 of the UL49 gene (SEQ ID No 1) with an oligonucleotide inserted at position 845 that encodes epitope tag sequences derived from the human cytomegalovirus UL83 gene (McLauchlan et al., 1994). Plasmid pVP22/159-259 was made by cleaving pYS360 with BssHII (position 803 in the UL49 sequence, SEQ ID No 1) and BamHI (a site which lies immediately upstream of the T7 terminator) and replacing the fragment with an oligonucleotide which specifies amino acid residues 254 to 259 immediately followed by a translational stop codon. Plasmid pVP22/172-259 was constructed by cleaving pVP22/159-259 with MscI (position 561 in SEQ ID No 1) and NdeI, filling in the overhanging 5 termini and ligation. Plasmids pVP22/159-301 and pVP22/159-301mut were made by inserting 460 bp MscI/EagI DNA fragments from pUL49ep (Leslie et al., 1996) and pUL49insl94 (Leslie, 1996) respectively into pYS360 which had been cleaved with MscI and NotI. Insertion of these fragments extended the region of VP22 expressed to the end of the open reading frame (amino acid 301). In both constructs, the HCMV UL83 epitope tag was present following the VP22 sequences. pVP22/159-301mut also contained an oligonucleotide which encoded 4 amino acid residues that were inserted at the codon specifying amino acid 194 (nucleotide position 626, SEQ ID No 1; Leslie, 1996).

(ii) VP16 constructs. Plasmid pETVP16 was used to express full-length VP16 under the control of the T7 RNA polymerase promoter (Arnosti et al., 1993). The truncated form of VP16 was expressed from a plasmid termed pETVP16trunc (a gift from Dr C. Preston). To construct pETVP16trunc, a partially self-complementary oligonucleotide (5' GATCTAGTGAGAGCTCACTA-3'), yielding four overhanging bases at each end, was inserted into the unique BamHI site in pMC1Δin15-17. This plasmid lacks the VP16 sequences between the linker insertion sites in pMC1in115 and pMC1in17 (Ace et al., 1988) with the BamH1 site lying immediately after the codon specifying residue 412. The VP16 sequences were then introduced into plasmid pET8c to give pETVP16trunc.

(iii) GST-gB construct. The parent plasmid used to express the cytoplasmic tail of gB was pGex2TNMCR (a gift from Dr R Everett; Meredith et al., 1994) which is a derivative of a commercially available construct pGex2T (Pharmacia). To construct pGex2TN.gB a MaeII/MseI fragment (encompassing residues 53404 to 53044 on the HSV-1 genome; McGeoch et al., 1988) from plasmid pGX135 (consists of the HSV-1 KpnI n fragment in vector pAT153) was inserted into the SmaI site of pGex2TNMCR. Insertion of this fragment at the SmaI site linked residues 798 to 904 of gB to the glutathione-S-transferase (GST) protein expressed by pGex2TNMCR.

Antibodies.

The mouse monoclonal antibody 9220 (DuPont Ltd, UK) recognises a 10 amino acid epitope derived from the HCMV UL83 gene product, which was used to tag VP22 sequences. For detection of VP16, the mouse monoclonal antibody LP1 (a gift from A. Minson; McLean et al., 1982) was used. The GST-gB fusion protein was detected using the IgG fraction of rabbit antiserum raised against glutathione-S-transferase (Sigma). Unless otherwise stated, all antibodies were used at dilutions of 1:1000.

Bacterial Strains.

The VP16 and VP22 proteins were made in E.coli strain BL21(DE3). The bacterial strain used to produce GST-gB was E.coli strain DH5a.

Production and Purification of Truncated Forms of Histidine-Tagged VP22.

BL21(DE3) cells containing the relevant plasmid DNA were grown overnight in 10 ml of YT medium containing 50 µg/ml kanamycin. This culture was transferred to 1 liter of YT medium and grown for 3 hours at 37° C. To induce protein expression, the culture was put on ice for 3–5 minutes, IPTG was added to a final concentration of 50 µM and the culture was incubated overnight at 15° C. Cells were spun down at 4,000 g for 10 minutes and the pellet was resuspended in 30 ml binding buffer (20 mM Tris-HCl, pH 8.0, 500 mM NaCl, 5 mM imidazole). The bacterial suspension was sonicated and centrifuged at 23,500 g for 20 minutes. The supernatant (called crude extract) containing the induced protein was retained for further purification.

Proteins containing the histidine tag were purified by binding to nickel nitrilotriacetic acid resin (Ni-NTA, Qiagen). Crude extract was added to resin which had been equilibrated with binding buffer and binding of the His-tagged VP22 to the resin occurred for 40 min at 4° C. The resin was spun down at 800 g for 5 minutes, washed four times (20 minutes per wash) in 50 ml binding buffer and transferred to a column. To elute histidine-tagged proteins, resin was washed with solutions containing increasing concentrations of imidazole which competitively removes the bound proteins. Solutions containing 60 mM imidazole, followed by 100 mM and 200 mM imidazole in 20 mM Tris-HCl, pH 8.0, 500 mM NaCl were used. 1 ml aliquots were collected and the amount of protein was determined by O.D. measurement at 280 nm. Protein was dialysed against 20 mM Tris-HCl, pH 8.0, 250 mM NaCl and concentrated at 7000 g using Centricon 10 microconcentrators (Amicon).

Production and Purification of VP16.

BL21(DE3) cells containing the relevant plasmid DNA were grown overnight in 10 ml or 100 ml YT medium containing 250 µg/ml ampicillin. These cultures were transferred to either 1 liter or 10 liters of YT medium and grown at 37° C. until the O.D. measured 0.5. To induce protein expression, IPTG was added to a final concentration of 1 mM and the culture was incubated for 2 hours at 26° C.

For studies of the interaction of VP22trunc with VP16 in solution, VP16 was partially purified from bacteria. Cells were spun down at 4,000 g for 10 minutes and lysed by sonication in 50 mM Tris-HCl, pH 8.2, 100 mM $Na_2SO_4$, 1 mM DTT, 10% glycerol, 0.1% CHAPS, 1 mM EDTA and 1 mM PMSF. The lysate was dialysed at 4° C. against 50 mM Tris-HCl, pH 8.2, 100 mM $Na_2SO_4$, 1 mM DTT, 10% glycerol, 0.1% CHAPS, 1 mM EDTA and then clarified by centrifugation at 17,500 g. Soluble VP16 protein was partially purified by ion-exchange FPLC on a Mono Q column (Pharmacia) using a NaCl gradient from 50 mM to 500 mM. Fractions containing VP16 were identified by Western blot analysis using LP1 antibody. Peak fractions were dialysed against 20 mM Tris-HCl, pH8.0, 250 mM NaCl at 4° C. and used thereafter without further purification.

For preparation of pure VP16 and truncated VP16 (VP16trunc), bacteria were grown, induced and lysed as described above; however, the extracts were partially purified by precipitation with 30% w/v ammonium sulphate. Precipitated protein was resuspended in 50 mM MES (2-[N-morpholino]ethane sulphonic acid), pH 6.5, 50 mM NaCl, 100 mM $Na_2SO_4$, 10% glycerol, 0.1% CHAPS and applied to a Mono S ion exchange column (Pharmacia). Protein was eluted by increasing the concentration of NaCl. Fractions containing VP16 were identified and dialysed as described above. The purity of protein was assessed to be >95% based on Coomassie Brilliant blue staining of denaturing polyacrylamide gels.

Production and Purification of GST-gB.

DH5α cells containing pGex2TN.gB plasmid were grown overnight at 37° C. in YT broth containing 100 µg/ml ampicillin. 6 ml of overnight culture was used to seed a 500 ml culture of YT broth and this was shaken at 37° C. for 4 hours. To induce expression of the fusion protein, IPTG was added to 0.1 mM and incubation at 37° C. was continued for 1 hour.

To prepare a crude extract, bacteria were pelleted by centrifugation at 5,000 g for 15 minutes and the pellet was resuspended in 12 ml PBSA containing 1 mM PMSF and lmM EDTA. The resuspension was frozen at −20° C., thawed and then sonicated. The sonicated suspension was incubated on ice and Triton X-100 was added slowly to a final concentration of 1% over a period of 20 minutes. Insoluble material was removed by centrifugation at 10,000 g for 10 minutes at 4° C. and the supernatant, which was termed crude extract, was stored at −20° C.

For purification of GST-gB, a column of glutathione-agarose (Sigma), swollen and equilibrated in PBSA, was prepared and washed with 10 volumes of a solution of PBSA, 1% Triton X-100, 1 mM PMSF and 1 mM EDTA. Crude extract was passed through the column which was then washed with 10 vols. of PBSA. Bound protein was eluted with 50 mM reduced glutathione in 400 mM Tris-HCl, pH 8.0 and peak fractions containing GST-gB were stored at −20° C. Prior to probing membranes in Far Western studies, fractions were pooled and dialysed against PBSA containing a protease inhibitor cocktail (Boehringer).

Synthesis and Purification of Oligopeptides. Peptides were synthesised by continuous flow Fmoc chemistry (Atherton and Sheppard, 1989; McLean et al., 1991) and, where stated in the text, were purified by preparative reverse-phase HPLC (Owsianka et al., 1993). The Mr values of peptides were determined by fast atom bombardment mass spectrometry (M-Scan) and corresponded to the predicted values. Peptides were dissolved in 20 mM Tris-HCl, pH 8.0, 250 mM NaCl and centrifuged at 11,500 g for 1 minute prior to use. Precipitates were observed with peptides D, E, and G and these peptides were classified as partially insoluble (Table 1). Precipitates were removed by centrifugation before use.

mM β-mercaptoethanol, 10% glycerol, 0.002% bromophenol blue) followed by heating to 100° C. for 5 minutes. For peptide studies, peptides were dissolved in 20 mM Tris-HCl, pH8.0, 250 mM NaCl at a concentration of 2 mg/ml. Incubation of peptides with partially purified VP16 extracts was performed at ambient temperature for 2 hours prior to the addition of VP22trunc. Samples were electrophoresed on denaturing polyacrylamide gels.

Polyacrylamide Gel Electrophoresis.

Proteins were separated on gels containing 10%, 12% or 15% acrylamide cross-linked with 2.5% (wt/wt) N,N' methylene bis-acrylamide. Polymerisation was initiated by addition of 0.04% TEMED and 0.06% APS. Samples were heated to 100° C. for 5 min in boiling mix prior to loading on the gel. Electrophoresis was performed for approximately 1 hour at 120–150 V or overnight at 40 V using the buffer system of Laemmli (1970). Proteins were detected by staining with Coomassie Brilliant blue for 20 minutes followed by destaining, or were transferred to nitrocellulose membrane for further analysis.

Western Blot Analysis.

Following electrophoresis proteins were electrotransferred at 4° C. to nitrocellulose membrane (Hybond ECL, Amersham) in blotting buffer (25 mM Tris-HCl, pH 8.3, 192 mM glycine, 20% methanol) for 5–6 hours at 50 mA. The membrane was then blocked overnight in TBS (20 mM Tris-HCl, pH 7.5, 500 mM NaCl) containing 3% gelatin. This was followed by incubation with the appropriate antibody at a dilution of 1:1000 in TTBS (TBS containing 0.05% Tween 20) containing 1% gelatin for 1.5–2 hours. The membrane was washed extensively with TTBS and bound antibody was detected by goat anti-mouse antibody (Sigma) at a dilution of 1:1000 in TTBS, 1% gelatin. After incubation for 1 hour with the secondary antibody, the

TABLE 1

Sequences and properties of the synthetic peptides derived from the VP22trunc sequence

| Peptide | Sequence | SEQ ID No | Mol. Wt. (Da) | Purity (%) | Solubility |
|---------|----------|-----------|---------------|------------|------------|
| A | GSHMARTAPTRSKTPAQGLA | 4 | 2037 | 87.8 | soluble |
| B | KTPAQGLARKLHFSTAPPNP | 5 | 2130 | 81.3 | soluble |
| C | FSTAPPNPDAPWTPRVAGFN | 6 | 2141 | 85.7 | soluble |
| D | TPRVAGFNKRVFCAAVGRLA | 7 | 2132 | 55.1 | partly soluble |
| E | CAAVGRLAAMHARMAAVQLW | 8 | 2125 | 58.8 | partly soluble |
| F | RMAAVQLWDMSRPRTDEDLN | 9 | 2403 | 99.0 | soluble |
| G | PRTDEDLNELLGITTIRVTV | 10 | 2254 | 62.2 | partly soluble |
| H | ITTIRVTVCEGKNLLQRANE | 11 | 2257 | 90.4 | soluble |
| I | NLLQRANELVNPDVVQDVPD | 12 | 2247 | 72.6 | soluble |
| J | DVVQDVPDPERKTPRVTGG | 13 | 2065 | 93.7 | soluble |

Co-purification of VP16 with VP22trunc on Ni-NTA Resin. Purified VP22trunc and a partially purified extract containing VP16, both in 20 mM Tris-HCl, pH8.0, 250 mM NaCl, were mixed at 4° C. for 15 to 30 minutes on a rotator. 50 μl of equilibrated Ni-NTA resin was added to each mixture and incubation was continued at 40C for a further 15 to 30 minutes. Resin was pelleted at 800 g for 1 minute and the supernatant (non-bound fraction) was removed. Resin was washed sequentially with 0.5 ml of 20 mM Tris-HCl, pH 8.0, 250 mM NaCl, 5 mM imidazole (twice) and 0.5 ml of 20 mM Tris-HCl, pH 8.0, 250 mM NaCl, 60 mM imidazole (four times). Bound protein was eluted by addition of 50 μl of boiling mix (160 mM Tris-HCl, pH 6.7, 2% SDS, 700 membrane was washed with TTBS and incubated with enhanced chemiluminescence (ECL) buffer (Amersham) for 2 minutes then exposed to XS-1 film (Kodak).

Far Western Blot Analysis.

Following electrophoresis, proteins were electrotransferred to either Hybond or ProBlott (Applied Biosystems) membrane and the membrane was incubated in renaturation buffer (50 mM Tris-HCl, pH 8.0, 150 mM NaCl, 10% glycerol, 1 mM DTT) at 4° C. for 5–6 hours.

For membranes probed with either VP16 or VP22trunc, blocking was performed overnight as described for Western blot analysis. Probing with epitope-tagged VP22 or VP16 was performed in 20 mM Tris-HCl, pH 8.0, 250 mM NaCl for 1.5 hours at ambient temperature. Excess probe was removed by washing 4 times (10 minutes per wash) in 20 mM Tris-HCl, pH8.0, 250 mM NaCl, followed by incubation with the appropriate antibody at a dilution of 1:1000 in TTBS/1% gelatin for 1.5–2 hours. Bound antibody was detected as described for Western blot analysis.

For membranes probed with GST-gB, blocking was performed overnight in PBSA containing 1% non-fat dried milk and 0.05% Tween 20 at 4° C. Membranes were then washed twice in renaturation buffer (10 min/wash) prior to incubation with fusion protein (final concentration 0.5 µg/ml) in renaturation buffer containing 1% BSA. Incubation was again performed overnight at 4° C. Following washing with renaturation buffer (four times, 10 minutes/wash) and a brief rinse with blocking buffer, the membrane was incubated with anti-GST antibody in PBSA, 1% non-fat dried milk, 0.05% Tween 20 and 1% BSA for 1 hour at ambient temperature. After four washes with PBSA, 0.05% Tween 20 (10 minutes/wash), bound antibody was detected with secondary antibody (goat anti-rabbit IgG, whole molecule; Sigma) conjugated to Horse Radish Peroxidase (HRP) by incubating at room temperature for 45 minutes. Following four further washes with PBSA, 0.05% Tween 20, the secondary antibody was visualised by enhanced chemiluminescence.

Fast Protein Liquid Chromatography (FPLC).

The sizes of proteins were determined on a Superdex 75 10/30 column (bed volume 24 ml; Pharmacia) which was equilibrated with 20 mM Tris-HCl, pH 8.0, 500 mM NaCl, 5% glycerol, 1 mM DTT. Protein samples, containing approximately 0.1–0.2 mg protein, were applied to the system in a volume of 200 µl. The samples were passed through the column at a flow rate of 1 ml/minute and protein was detected at 280 nm. Samples were collected in 0.2 ml fractions for further analysis.

Enzyme-Linked Immunosorbent Assays (ELISA).

Dilutions of proteins in PBS were coated overnight onto flat bottomed micro-titre plates (Dynatech) at 37° C. and then blocked with either 2% BSA or 10% new-born calf serum (NCS) in PBS for 1 hour at 37° C. Specific binding of a second protein to the plate-bound protein was performed for 1.5–2 hours at ambient temperature. a Excess secondary protein was removed by washing four times with PBS, 0.3% Tween 20. Bound protein was detected by incubation for 1.5–2 hours with LP1 antibody in PBS, 1% gelatin or PBS, 2% NCS. The bound antibody was detected by incubation for 1 hour at ambient temperature with anti-mouse antibody conjugated to HRP (1:500) and visualised with 5mg/ml enzyme substrate 2,2'-azino-bis(3-ethylbenzthiazoline-6-sulphonic acid) (ABTS; Sigma) in citrate-phosphate buffer containing 6 µl hydrogen peroxide in a total volume of 20 ml. Optical densities were measured on a Titertek Multiscan PLUS instrument.

RESULTS

1. Purification and Characteristics of Proteins Expressed in Bacteria (i) The Truncated Forms of VP22.

Previous results had shown that VP16 and VP22 interact in HSV-1-infected cells (Elliott et al., 1995). This interaction was reproduced in biochemical studies in which in vitro-translated VP22 was co-purified on glutathione-Sepharose beads using a glutathione-S-transferase-VP16 fusion protein that had been expressed in bacteria. To further characterise the region within VP22 to which VP16 bound, a truncated form of VP22, termed VP22trunc, which contained residues 159–267 of the protein was expressed in bacteria. For purification and detection purposes, this segment of protein was flanked at the N-terminus with a stretch of 22 amino acids which contained 6 consecutive histidine residues and at the C-terminus by 13 amino acids that constituted an epitope tag derived from the human cytomegalovirus (HCMV) pp65 protein (FIG. 1B: SEQ ID No 3); the histidine residues allowed purification of the protein on Ni-NTA resin and the epitope tag could be recognised by a monoclonal antibody termed 9220. This expression system yielded approximately 5–8 mg of protein per liter of bacterial culture. From analysis of the proteins eluted from Ni-NTA resin at different concentrations of imidazole, effectively pure, soluble protein (>95% as determined by Coomassie Brilliant blue staining of polyacrylamide gels) was obtained by elution with buffer containing 100 mM imidazole. The authenticity of VP22trunc was determined by Western blot analysis using antibody 9220 (FIG. 5A, Lane 4) and by mass spectrometry (data not shown). Analysis of the molecular weight of native VP22trunc by size exclusion chromatography showed that approximately 70% of the protein made in bacteria was 33 KDa with the remaining 30% having a higher molecular weight (FIG. 2). Thus, most of the VP22 has a molecular weight that corresponds exactly to twice the predicted size of monomeric protein and it was concluded that this 33 KDa species was a dimer. The higher molecular weight material is considered to be a mixture of oligomeric forms of VP22trunc.

In addition to VP22trunc, four other truncated forms of VP22 were produced in bacteria (Table 2). The constructs which permitted synthesis of these polypeptides are described in Methods. Each protein was purified using identical expression and purification methods as for VP22trunc. The only changes in characteristics observed were with VP22/159-259 and vP22/172-259 which eluted more efficiently from Ni-NTA resin in buffer containing 200 mM imidazole, and yields of vP22/172-259 were much lower, probably due to difficulties with solubility.

TABLE 2

Features of the truncated forms of VP22 expressed in bacteria

| VP22 Polypeptide | Mol.Wt.(KDa) | Residues Expressed | Tag Attached to Protein |
|---|---|---|---|
| VP22trunc | 16 | 159–267 | HCMV[a] + histidine |
| VP22159-301 | 20 | 159–301 | HCMV[a] + histidine |
| VP22159-301mut | 20.5 | 159–301 (4 amino acid insertion at 194) | HCMV[a] + histidine |
| VP22159-259 | 14 | 159–259 | histidine |
| VP22172-259 | 12 | 172–259 | histidine |

[a]denotes the HCMV epitope tag (ii) VP16.

Figure 5A:
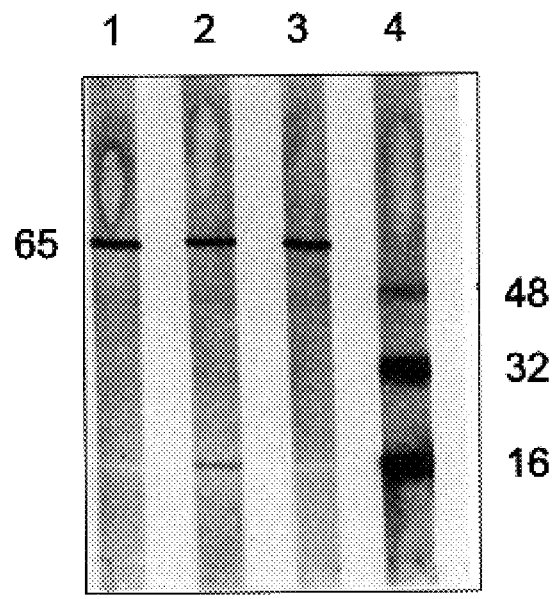

Two forms of VP16 were produced for studies on interactions with VP22. The first of these was full-length VP16 which was prepared in both partially purified and fully purified states (see Methods). Purified VP16 was shown to be authentic by Western blot analysis with monoclonal antibody LP1 (Fig 5A, lane 1). In partially purified extracts, VP16 could be identified as a 65 KDa species on Coomassie Brilliant blue-stained polyacrylamide gels (FIG. 4, lane 2). The truncated form of VP16, VP16trunc was produced from plasmid pETVP16trunc in which the sequences encoding residues 413 to 490 are not expressed. This VP16 product was purified to homogeneity in the same way as full length VP16 and was recognised by LPI antibody (data not shown).

(iii) GST-gB.

The C-terminal amino acids of gB represent a charged domain of protein which is located internally in the virus particle and hence may interact with tegument proteins underlying the virus envelope. To examine possible interactions with tegument proteins, and for purification and detection purposes, these residues were linked to the GST protein which has a size of 26 KDa. Thus, the predicted size of the fusion protein was about 37 KDa. Following purification on glutathione-agarose beads, two polypeptides with apparent molecular weights of about 35 KDa and 28 KDa were detected (FIG. 3, lanes 6 and 7); the upper species approximates to the predicted size for the GST-gB fusion protein while the lower band has an identical apparent molecular weight to GST protein (lanes 8 and 9). To further verify that the 35 KDa species was the fusion polypeptide, Western blot analysis showed that anti-GST antibody recognised this protein (data not shown). Furthermore, the nucleotide sequence of the region containing gB sequences in pGex2TN.gB was determined. This revealed no nucleotide changes as compared to the published sequence and verified that the gB sequences were in the same open reading frame as those for the GST gene. Therefore, it was concluded that the 35 KDa and 28 KDa species were the GST-gB fusion product and the GST protein respectively. It was assumed that the latter product was generated by proteolytic cleavage of the fusion protein between the GST and gB domains which may have occurred during synthesis in bacteria. This is a consistent feature found in systems over-expressing GST fusion proteins. Both species were routinely found in purified preparations of the fusion protein and the relative proportions of each were 1:1. The concentration of GST-gB in this preparation, which was used in the experiments presented in Section 4, was about 250 µg/ml based on comparison with standard amounts of BSA protein (FIG. 3, lanes 1-4).

2 In Vitro Analysis of the Interaction Between VP16 and VP22trunc.

(i) Co-purification of VP16 and VP22trunc on Ni-NTA Resin

The ability of VP16 to interact with VP22trunc was examined by mixing purified VP22trunc with a bacterial extract containing VP16 (FIG. 4, lane 1) followed by analysis of the polypeptides retained on Ni-NTA resin (FIG. 4). Results revealed that in the absence of VP22trunc, several polypeptides were eluted from the resin (FIG. 4, lane 14). In the presence of VP22trunc, a novel band of 65 KDa also co-eluted (FIG. 4, lane 13); Western blot analysis showed that this polypeptide corresponded to VP16 (data not shown). This ability to specifically elute VP16 only in the presence of VP22trunc was reproducible over several experiments using various quantities of VP22trunc and crude bacterial extract containing VP16. From these data, it was concluded that the co-elution of VP16 with VP22trunc from Ni-NTA resin resulted from the specific interaction between these proteins.

(ii) Detection of VP22trunc by VP16 using Far Western Analysis

Previous investigations made use of Far Western analysis to study the interaction between VP16 and VP22 (Elliott et al., 1995). In those studies, various forms of VP16 were separated by electrophoresis, blotted onto nitrocellulose filters and renatured. The blot was then probed with in vitro translated radio-labelled VP22 to detect binding to VP16. To extend our studies, Far Western analysis was used to examine whether this interaction could be studied with VP22trunc attached to the blot and VP16 used as a probe. Binding of VP16 to proteins on the blot could then be detected using LPI antibody. In FIG. 5A, purified VP22trunc has been added to a bacterial extract containing VP16 and the proteins electrophoresed on a polyacrylamide gel followed by transfer to membrane. Probing individual strips from the membrane separately with LP1 and 9220 antibodies reveals the positions of VP16 (lane 1) and VP22trunc respectively (lane 4). In addition to monomeric VP22trunc, antibody 9220 also recognises the dimer and trimer forms of the protein; the presence of dimers in particular was a consistent observation and these are thought to arise through incomplete denaturation of the native protein. Incubation of a portion of the blot with VP16 followed by LP1 reveals that not only does the antibody detect a 65 KDa protein corresponding to VP16 but also a band corresponding to monomeric VP22trunc (lane 2). Therefore, these data show that VP16 can recognise VP22trunc immobilised on membrane. In the converse experiment, VP22trunc can also bind to immobilised VP16 (data not shown). To confirm the binding specificity of VP16 for immobilised VP22trunc, a portion of the blot was probed with the VP16trunc. No binding of VP16trunc to VP22trunc could be detected (lane 3). These data confirm that removal of the C-terminal residues of the VP16 significantly reduces the ability of VP16 to bind to VP22 (Elliott et al., 1995) and demonstrate the specific nature of the interaction between the proteins using this form of analysis.

Figure 5B:
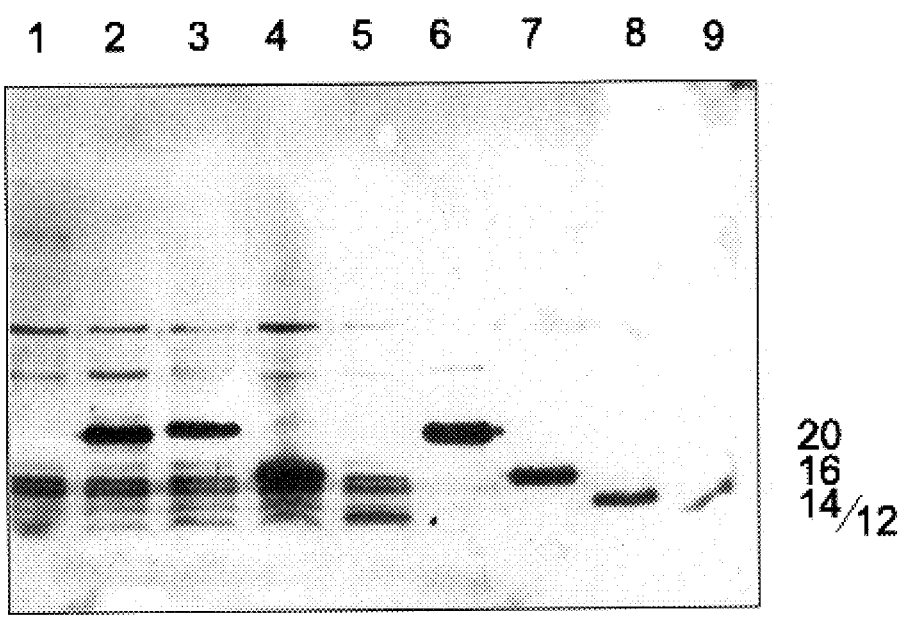

To further define the region of VP22 involved in VP16 binding, studies were performed with additional forms of bacterially-expressed VP22, two of which lacked the C-terminal epitope tag (Table 2). Both purified and crude extracts of all the available forms of VP22 made in bacteria were electrophoresed on a polyacrylamide gel and transferred to nitrocellulose membrane along with an uninduced bacterial extract. The blot was incubated with VP16 and bound protein was detected with LP1. VP16 was able to associate with all of the VP22 species (Fig SB, lanes 2 to 9). Furthermore, a polypeptide which contained residues 159–301 and had an insertion of 4 amino acids at position 194 was recognised by VP16 (FIG. 5B, lane 3). The additional bands detected in crude extracts containing the VP22 proteins were present also in the uninduced control sample (compare lane 1 with lanes 2–5). These data indicate that an amino acid sequence responsible for specifically binding VP16 lies between residues 172 and 259 of VP22 and that the epitope tag is not involved in the interaction.

(iii) Binding of VP16 to VP22trunc by ELISA

To adopt a more quantitative approach, an ELISA for VP16 binding to VP22trunc was developed. Optimal conditions were determined by coating wells with various quantities of VP22trunc followed by blocking with 2% BSA. Plates were then incubated with dilutions of VP16 and the bound VP16 detected with LP1. This showed specific detection of VP16 binding at a range of concentrations of VP16 and VP22trunc (FIG. 6). Based on these data and repeat experiments (data not shown), the concentrations of VP16 and VP22trunc used in subsequent assays were 1.64 g/ml and 3.2 µg/ml respectively (FIG. 6, arrow).

3 Disruption of the VP16/VP22 Interaction by Synthetic Peptides

Figures 1A, 1B:
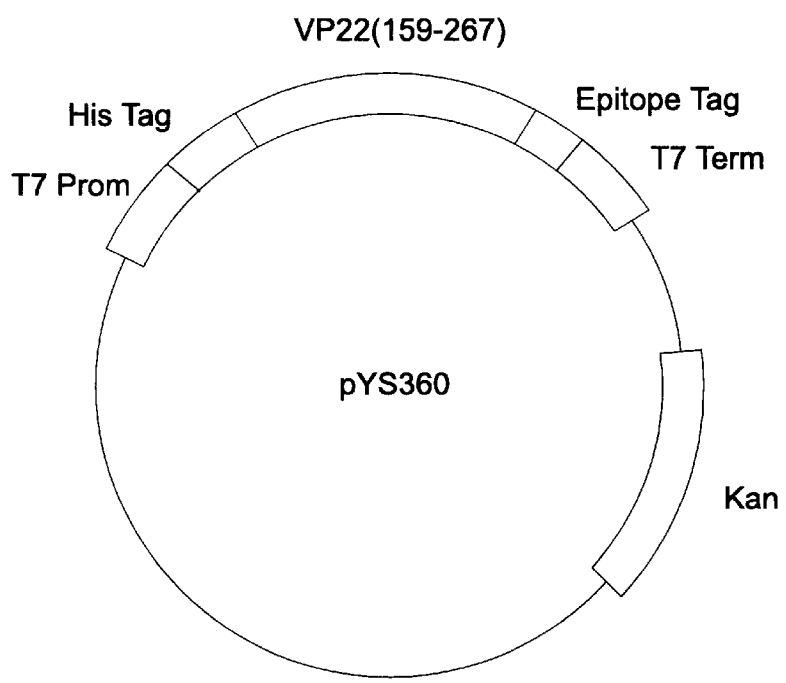
FIG. 1 (A) Relevant features of the pYS360 construct. The map shows the locations of the T7 promoter and terminator sequences which control expression of VP22trunc. The order of the elements which-comprise VP22trunc is shown and Kan represents the position of the kanamycin resistance gene.

To further examine the region within VP22 to which VP16 binds and to determine whether interaction between the proteins could be interrupted, a series of ten peptides were synthesised based on the predicted sequence of the VP22trunc polypeptide between residues 18 and 144 (Fig 1B; SEQ ID No 3); this region encompasses the VP22 and epitope tag sequences in VP22trunc. Each peptide was 20 amino acids in length with an overlap of 8 residues between adjacent peptides. Relevant characteristics of the is peptides synthesised are given in Table 1.

(i) Inhibition of the VP16/VP22trunc Interaction in Co-purification Studies.

Results presented in Section 2(i) had shown that VP16 co-elutes from Ni-NTA resin in the presence of VP22trunc and it was concluded that this indicated interaction between these polypeptides. The ability of synthetic peptides to inhibit this interaction was analysed by mixing them individually with the partially purified VP16 extract prior to addition of VP22trunc. From the intensity of the 65 KDa species in the crude extract (FIG. 4, lane 2), it was estimated that the concentration of VP16 was approximately 0.5 nM. To ensure that experiments were performed in an excess of peptide, peptides were prepared at a concentration of 2 mg/ml (about 1 mM) and equal volumes of peptide and extract were mixed. This gave a relative molar ratio of VP16 to peptide of 1:300. However, it should be noted that certain peptides were not completely soluble (Table 1) and in those cases, the ratio would be reduced. Analysis of the proteins which co-elute with VP22trunc in the presence of each of these peptides is shown in FIG. 4. This revealed that VP16 failed to co-elute with VP22trunc following incubation with peptide E (lane 7) and in reduced amounts in the presence of peptide D (lane 6). By contrast, no quantitative differences in the amount of VP16 which co-elutes were observed in the presence of the other peptides when compared to the control sample (compare lanes 3 to 5 and 8 to 12 with lane 13). This suggested that peptides D and E could inhibit binding between VP16 and VP22trunc. However, these peptide preparations were not homogeneous (Table 1) and may contain impurities which non-specifically inhibit the interaction. To eliminate this possibility, peptides D and E were purified to homogeneity by reverse phase HPLC and further analysis showed that their inhibitory capabilities were retained (data not shown).

(ii) Inhibition of the VP16/VP22trun=Interaction in Far Western Analysis.

Based on the studies with soluble VP16 and VP22trunc presented above, only a restricted number of peptides were examined by Far Western analysis to identify those that may prevent binding of VP16. Thus, VP22trunc was added to a crude extract of bacterially expressed VP16 and the proteins were electrophoresed on a polyacrylamide gel followed by transfer to a membrane. As shown in FIG. 7A, incubation of a portion of the blot with VP16 followed by LP1 antibody identified two bands, one of which corresponds to VP16. (compare lane 2 with lane 1) while the second is the monomeric form of VP22trunc (compare lane 2 with lane 4). Before the addition of VP16 the blot strips in lanes 3 to 8 were incubated with crude preparations of peptides C, D, E, or E' as well as mixtures of either 0 and E or C and F. When the blot strips were incubated with peptides C and F either singly or in combination, VP16 bindincg to VP22trunc was not prevented (FIG. 7A, lanes 3, 6 and 8). By contrast, incubation with peptides D and E either separately or as a mixture resulted in loss of recognition of VP22trunc (FIG. 7A, lanes 4, 5 and 7). In support of the co-purification studies in 2(i), these data suggest that peptides D and E can block binding of VP16 to immobilised VP22trunc. From Table 1 aLnd as described in above, impurities in peptides D an(i E could account for their inhibitory effects. Therefore, the experiment as shown in FIG. 7A was repeated with purified preparations of peptides D and E. Again, these peptides were able to block binding of VP16 to VP22trunc (FIG. 7B, lanes 4 and 5) while peptides C and F had no effect (FIG. 7B, lanes 3 and 6). The oligopeptide CAAVGRLA, comprising the overlap region between peptides D and E, may be particularly important in the VP16 binding function, and this oligopeptide, along with functional equivalents and substitutions thereof, forms a further aspect of the invention.

The results presented thus far have established that peptides D and E block the interaction between VP16 and VP22trunc. The inhibitory effect of the peptides was further tested to examine whether they were capable of blocking the interaction of VP16 with full-length VP22. Hence, an extract from vUL49ep light particles containing full length VP22 was electrophoresed on a polyacrylamide gel and the proteins w7ere then transferred to membrane. vUL49ep is a recombinant HSV-1 virus which expresses two forms of VP22; the first is the endogenous form which is unmodified and the second is an epitope-tagged version which is expressed under the control of the HCMV immediate early promoter (Leslie et al., 1996). Previous studies have indicated that the epitope-tagged version of VP22 is present in high amounts in vUL49ep virus particles (Leslie et al., 1996). Incubation of blot strips with antibodies LP1 and 9220 shows the positions of both VP16 and full-length VP22 respectively on the blot (FIG. 8, lanes 1 and 6). Probing with VP16 followed bit LP1 shows that the antibody detects, in addition to VP16, a band of 40 KDa which represents full-length tagged VP22 (FIG. 8, lane 2). This indicates that the residues containing the histidine tag present at the N-terminus of VP22trunc do not contribute to VP16 binding. Prior incubation with either peptide D or E completely blocks binding of VP16 to VP22 (FIG. 8, lanes 4 and 5). However, peptide C does not hinder the interaction (FIG. 8, lane 3). Thus, peptides D and E are sufficient to completely inhibit the recognition of both VP22trunc and full-length VP22 by VP16.

(iii) Inhibition of the VP16/VP22trunc Interaction in ELISAS.

The studies presented above have provided strong evidence in support of peptide inhibition of the interaction between VP16 and VP22. However, quantitative analysis of the ability of peptides to block any interaction is difficult to perform by the above methods. Therefore, using the ELISA system described in Results Section 2(iii) with the exception that PBS/10% NCS was utilised as a blocking agent, the inhibitory effects of peptides D and E were examined. This modification arose due to nonspecific binding of the peptides to wells when BSA was used for blocking (data not shown). Results showed that the addition of the pure preparations of either peptide D or E at concentrations of both 100 and 500 $\mu$g/ml could inhibit binding of VP16 to VP22trunc (FIG. 9). However, neither peptides B, C nor F had any effect on interaction between the proteins (FIG. 9). 50% inhibition of VP16 binding was observed at concentration, of 212.5 $\mu$g/ml for peptide D and 85.7 $\mu$g/ml for peptlde E. These correspond to molarities of 99.7 $\mu$M anti 44.1 $\mu$M respectively for these peptides. It should be noted however, that these concentrations represent maximum molarities, since the peptides were not 100% soluble even following purification.

(iv) Direct Binding of Peptides D anii E to VP16.

To examine whether VP16 could bind directly to the peptides, wells were coated with each peptide (A–J) at a range of concentrations from 1 g/ml to 500 $\mu$g/ml and the plate was then blocked with PBS/13% NCS. Incubation with VP16 showed that binding did not occur with peptides A, B, C, F, G, I and J (FIG. 10). However, binding was found with higher concentrations of peptides D and E (FIG. 10). In addition, there was evidence also for VP16 binding to peptide H; the nature of this interaction was not further examined. Nonetheless, the data for peptides D and E implicate direct binding of these peptides to VP16 as the mechanism for inhibiting its interaction with VP22. Peptide H also was active in experiments which prevented gB binding to VP22trunc [Section 4 (iii)] and thus also forms an aspect of the invention.

4 In vitro Binding of gB to VP22 and Disruption of Binding by Synthetic Peptides.

(i) Structural Proteins Recognised by GST-gB using Far Western Blot Analysis.

In a previous study with cross-linking reagents, gB was found to be in close proximity to four structural proteins in virions (Zhu and Courtney, 1994). Three of these proteins were proposed to be the tegument components, VP11/12, VP13/14 and VP16 although VP16 was the only species positively identified by reactivity with a specific antibody. The fourth polypeptide had a similar molecular weight to VP22 but was not considered to be a tegument protein. Since the tegument underlies the envelope, it is reasonable to conclude that the endodomains of glycoproteins will contact the tegument. To analyse whether the C-terminal residues of gB, which constitute the endodomain of the polypeptide, could interact with any structural components, Far Western blot analysis was performed using purified HSV-1 virions with GST-gB as a probe. FIG. 11, lane 1 shows that a series of bands were identified following detection of bound GST-gB with anti-GST antibody. The major species had apparent molecular weights of 120 KDa, 90 KDa, 82 KDa, 65 KDa and 38 KDa; similar data have also been obtained with L-particles (lane 3). Control experiments revealed that the 65 KDa band is a non-specific species which was also detected using GST protein as a probe (lane 2). Further data (not shown) have shown that the 90 KDa and 82 KDa bands are VP11/12 (encoded by UL46) and VP13/14 (encoded by UL47) respectively. This agrees with the results obtained in the cross-linking studies performed by Zhu and Courtney (1994) although there is no evidence here that GST-gB associates with VP16. Presently, the 120 KDa band has not been characterised. In agreement with the data presented by Zhu and Courtney (1994), the 38 KDa species has an identical molecular weight to VP22. To further characterise this species, GST-gB was used to probe L-particles made by vUL49ep which contains epitope-tagged VP22 and, moreover, the tagged VP22 is present in greater quantities when compared with virus particles made by wild-type virus. This showed that GST-gB bound to the same species as identified with wild-type virions and, in addition, bound to tagged vP22 which has a slightly higher molecular weight than the natural protein (FIG. 11, lane 3). Another experiment using L-particles made by a virus recombinant, vUL49Δ268-301, in which the C-terminal 34 residues have been removed from the tagged copy of the UL49 gene, showed that GST-gB bound to this truncated form of VP22 (FIG. 11, lane 4). This provides direct evidence that the C-terminal region of gB interacts with VP22, and moreover that the C-terminal 34 residues of VP22 are not required for binding to gB.

(ii) Binding of gB to VP22trunc.

The above analysis demonstrated that gB binds specifically to VP22 and to a C-terminally truncated form of the protein. The ability of gB to associate with the bacterially-expressed form of VP22, VP22trunc, was then studied. As shown in FIG. 12A, lane 1, three bands of 65 KDa, 25 KDa and 16 KDa were detected following incubation with GST-gB and anti-GST antibody. Of these three species, the 65 KDa and 25 KDa bands also were evident in the control using GST protein and anti-GST antibody (FIG. 12A, lane 2). However, the 16 KDa protein was not observed and analysis with 9220 MAb indicated that this polypeptide was VP22trunc (FIG. 12A, lane 3). Hence the region of VP22 consisting of amino acids 159-267 not only binds VP16 but also interacts with the C-terminal residues of gB.

(iii) Inhibition of gB/VP22trunc Binding by Synthetic Peptides.

Similar to the studies performed with inhibition of binding of VP16 to VP22, peptides A to J, which span residues 18 to 144 of VP22trunc, were used to examine whether gB binding could also be prevented (FIG. 12B). Co-incubation of individual peptides with GST-gB showed that peptides D, E and H completely inhibited binding of gB (lanes 5, 6 and 9; these inhibitory effects were reproducible in other experiments. The data presented in Section 3(i-iii) also indicate that peptides D and E inhibit the interaction between VP16 and VP22 while there is evidence that peptide H can bind VP16 [Section 3(iv)]. This suggests that these peptides have the ability, to interact not only with VP16, but also with the C-terminal domain of gB.

Modifications and improvements can be incorporated without departing from the scope of the invention.

REFERENCES

Ace, C. I., Dalrymple, M. A., Ramsay, F. H., Preston, V. G. and Preston, C. M. (1988). Mutational analysis of the herpes simplex virus type I trans-inducing factor Vmw65. *Journal of General Virology* 69; 2595–2605.

Arnosti, D. N., Preston, C. M., HagmanrL, M., Schaffner, W., Hope, R. G., Laughlan, G. and Luisi, B. F. (1993). Specific transcriptional activation in vitro by the herpes simplex virus protein VP16. *Nucleic Acids Research* 21; 5570–5576.

Atherton, E. and Sheppard, R. C. (editors) (1989). *Solid Phase Peptide Synthesis: A Practical Approach*. Oxford: IRL Press.

Blaho, J. A., Mitchell, C. and Roizmar, B. (1994). An amino acid sequence shared by the herpes simplex virus 1 alpha-regulatory proteins 0, 4, 22 and 27 predicts the nucleotidylylation of the UL21, UL31, UL47 and UL49 gene products. *Journal of Biological Chemistry* 269; 17401–17410.

Bond, V. C., Person, S. and Warner, S. C. (1982). The isolation and characterization of mutants of herpes simplex virus type 1 that induce cell fusion. *Journal of General Virology* 61; 245–254.

Brown, S. M.; Ritchie, D. A. and Subak-Sharpe, J. H. (1973). Genetic studies with herpes simplex virus type 1. The isolation of temperature-sensitive mutants, their arrangement into complementation groups and recombination analysis leading to a linkage map. Journal of General Virology 18; 329–346.

Cai, W., Gu, S. and Person, S. (1988). Role of glycoprotein B of herpes simplex virus type 1 in viral entry and cell fusion. *Journal of Virology* 62; 2596–2604.

Ejercito, P. M., Kieff, E. D. and Roizrian, B. (1968). Characterization of herpes simplex virus strains differing in their effects on social behaviour of infected cells. *Journal of General Virology* 2; 357–364.

Elliott, G. D. and Meredith, D. M. (1992). The herpes simplex virus type 1 tegument protein VP22 is encoded by gene UL49. *Journal of General Virology* 73; 723–726.

Elliott, G., Mouzakitis, G. and O'Hare, P (1995). VP16 interacts via its activation domain with VP22, a tegument protein of herpes simplex virus, and is relocated to a novel macromolecular assembly in coexpressing cells. *Journal of Virology* 69; 7932–7941.

Elliott, G and O'Hare, P. (1997). Intercellular trafficking and protein delivery by ii herpesvirus structural protein. *Cell* 8, 223–23.3.

Gage, P. J., Levine, M. and Glorioso, J. C. (1993). Syncitium-inducing mutations localize to two discrete regions within the cytoplasmic domain of herpes simplex virus type 1 glycoprotein B. *Journal of Virology* 67; 2191–2201.

Highlander, S. L., Goins, W. F., Person, S., Holland, T. C., Levine, M. and Glorioso, J. C. (1991). Oligomer formation of the gB glycoprotein of Herpes simplex virus type 1 *Journal of Virology* 65; 4275–4283.

Knopf, K. W. and Kaerner, H. C. (1980). Virus-specific basic phosphoproteins associated with herpes simplex virus type 1 (HSV-1) particles and the chromatin of HSV-1-infected cells. *Journal of General Virology* 46; 405–414.

Liang, X., Chow, B., Li, Y., Raggo, C., Yoo, D., AttahPoku, S., and Babiuk, L. A. (1995). Characterization of bovine herpesvirus 1 UL49 homolog gene and product: bovine herpesvirus 1 UL49 homolog is dispensable for virus growth. *Journal of Virology* 69; 3863–3867.

Laemmli, U. K. (1970). Cleavage of structural proteins during the assembly of the head of bacteriophage T4. *Nature, London* 227; 680–685.

LaQuerre, S., Person, S. and Glorioso, J. C. (1996). Glycoprotein B of herpes simplex virus type 1 oligomerizes through the intermolecular interaction of a 28-amino-acid domain. *Journal of Virology* 70; 1640–1650.

Leslie, J. (1996). An investigation into factors that influence the incorporation of proteins into the HSV-1 tegument. PhD Thesis, University of Glasgow.

Leslie, J., Rixon, F. J. and McLauchlan, J. (1996). Overexpression of the herpes simplex virus type 1 tegument protein VP22 increases its incorporation into the HSV-1 tegument. *Virology* 220; 60–68.

McGeoch, D. J., Dalrymple, M. A., Davison, A. J., Dolan, A., Frame, M. C., McNab., Perry, L. J., Scott, J. E. and Taylor, P. (1988). The complete DNA sequence of the long unique region in the genome of herpes simplex virus type 1. *Journal of General Virology* 69; 1531–1574.

McLauchlan, J., Addison, C., Craigie, M. C. and Rixon, F. J. (1992). Noninfectious L particles supply functions which can facilitate infection by HSV-1. *Virology* 190; 682–688.

McLauchlan, J. and Rixon, F. (1992). Characterisation of enveloped tegument structures (L particles) produced by alphaherpesviruses: integrity of the tegument does not depend on the presence of capsid or envelope. *Journal of General Virology* 73; 269–276.

McLauchlan, J., Liefkens, K. and Stow, N. D. (1994). The herpes simplex virus type 1 UL37 gene product is a component of virus particles. *Journal of General Virology* 75; 2047–2052.

McLean, C., Buckmaster, A., Hancock, D., Buchan, A., Fuller, A. and Minson, A. (1982). Monoclonal antibodies to three non-glycosylated antigens of herpes simplex virus type 2. *Journal of General Virology* 63; 297–305.

McLean, G. W., Owsianka, A. M., Subak-Sharpe, J. H. and Marsden, H. S. (1991). Generation of anti-peptide and anti-protein sera: effect of peptide presentation on immunogenicity. *Journal of Immunological Methods* 137; 149–157.

Meredith, M., Orr, A. and Everett, R. (1994). Herpes simplex virus type 1 immediate-early protein Vmw110 binds strongly and specifically to a 135-KDa cellular protein. *Virology* 200; 457–469.

O'Hare, P. (1993). The virion transactivator of herpes simplex virus. *Seminars in Virology* 4; 145–155.

Owsianka, A. M., Hart, G., Murphy, M., Gotlieb, J., Boehme, R., Challberg, M. and Marsden, H. S. (1993). Inhibition of herpes simplex virus type 1 DNA polymerase activity by peptides from the UL42 accessory protein is largely non-specific. *Journal of Virology* 67; 258–264.

Rixon, F. J. (1993). Structure and assembly of herpesviruses. *Seminars in Virology* 4; 135–144.

Rixon, F. J., Addison, C. and McLauchlan, J. (1992). Assembly of enveloped tegument structures (L particles) can occur independently of virion maturation in herpes simplex virus type 1-infected cells. *Journal of General Virology* 73; 277–284.

Szilagyi, J. F. and Cunningham, C. (1991). Identification and characterisation of a novel non-infectious herpes simplex virus-related particle. *Journal of General Virology* 72; 661–668.

Weinheimer, S. P., Boyd, B. A., Durham, S. K., Resnick, J. L. and O'Boyle, D. R. (1992). Deletion of the VP16 open reading frame of herpes simplex virus type 1. *Journal of Virology* 66; 258–269.

Zhu, Q. and Courtney, R. J. (1994). Chemical cross-linking of virion envelope and tegument proteins of herpes simplex virus type 1. *Virology* 204; 590–599.

What is claimed is:

1. An antiviral agent which prevents maturation and/or replication of an alphaherpesvirus by inhibiting association of VP22 with VP16 and/or with gB, wherein said antiviral agent mimics a portion of HSV VP22, said portion being located at amino acids 159–301 of HSV VP22.

2. An antiviral agent as claimed in claim 1 which is a peptide having an amino acid sequence corresponding to the sequence of the C-proximal portion of VP22, wherein said C-proximal portion of VP22 is the 109 amino acid portion encoded by nucleotides 105590 to 105919 of HSV-1.

3. An antiviral agent as claimed in claim 1 which binds to at least a portion of the C terminus of gB and/or VP16.

4. An antiviral agent as claimed in claim 1, wherein said agent is a peptide having a sequence:
   a) TPRVAGFNKRVFCAAVGRLAAMHARMAAVQLW (SEQ ID No 14); or
   b) ITTIRVTVCEGKNLLQRANE (SEQ ID No 11); or
   c) a portion thereof.

5. An antiviral agent as claimed in claim 1 which is a synthetic peptide.

6. An antiviral agent as claimed in claim 1 which inhibits association of VP22 with VP16.

7. An antiviral agent as claimed in claim 1 which inhibits association of VP22 with gB.

8. A combination of an antiviral agent as claimed in claim 7 together with an antiviral agent which prevents maturation and/or replication of a herpesvirus by inhibiting association of VP22 with gB.

9. A combination of antiviral agents as claimed in claim 8 comprising:
   a) the peptide TPRVAGFNKRVFCAAVGRLA (SEQ ID No 7) or a portion thereof; or
   b) the peptide CAAVGRLAAMHARMAAVQLW (SEQ ID No 8) or a portion thereof,
together with the peptide ITTIRVTVCEGKNLLQRANE (SEQ ID No 11) or a portion thereof.

10. An assay to determine the ability of a test substance to interfere with the association of VP22 with VP16 or of VP22 with gB in an alphaherpesvirus, said assay comprising:
   i) providing a first viral component consisting of VP22;
   ii) providing a second viral component selected from the group consisting of gB and VP16;
   iii) exposing one of said first and second viral components to a test substance followed by the other of said first and second viral components, or exposing said first viral component to said second viral component followed by a test substance;
   iv) washing to remove any unassociated first or second viral component and/or test substance; and
   v) detecting the presence, and optionally determining the amount, associated first and second viral components.

11. An assay as claimed in claim 10 wherein one of said first and second viral components is localised on a surface.

12. An assay as claimed in claim 10 wherein an antibody is used to detect the presence of second viral component associated with said first viral component.

13. A method of preventing maturation of an alphaherpesvirus, the method comprising providing an agent which inhibits the interaction of gB and/or VP16 with VP22, adding said agent to said replicating alphaherpesvirus in sufficient quantity to cause said inhibition and monitoring the effect on viral replication and thus determining the presence or extent of said inhibition.

\* \* \* \* \*

SEQUENCE LISTING

```
<160> NUMBER OF SEQ ID NOS:   14

<210> SEQ ID NO 1
<211> LENGTH: 950
<212> TYPE: DNA
<213> ORGANISM: HERPESVIRUS TYPE 1

<400> SEQUENCE: 1
ggcctaattg tccgcgcatc cgaccctagc gtgttcgtgg aaccatgacc tctcgccgct      60
ccgtgaagtg cggtccgcgg gaggttccgc gcgatgagta cgaggatctg tactacaccc     120
cgtcttcagg tatggcgagt cccgatagtc cgcctgacac ctcccgccgt ggcgccctac     180
agacacgctc gcgccagagg ggcgaggtcc gtttcgtcca gtacgacgag tcggattatg     240
ccctctacgg gggctcgtca tccgaagacg acgaacaccc ggaggtcccc cggacgcggc     300
gtcccgtttc cggggcggtt ttgtccggcc cggggcctgc gcgggcgcct ccgccacccg     360
```

```
ctgggtccgg aggggccgga cgcacaccca ccaccgcccc ccggccccc cgaacccagc      420 gggtggcgac taaggccccc gcggccccgg cggcggagac cacccgcggc aggaaatcgg      480
cccagccaga atccgccgca ctcccagacg ccccgcgtc gacggcgcca acccgatcca      540
agacacccgc gcagggctg gccagaaagc tgcactttag caccgccccc ccaaaccccg      600
acgcgccatg gaccccccgg gtggccggct ttaacaagcg cgtcttctgc gccgcggtcg      660
ggcgcctggc ggccatgcat gcccggatgg cggcggtcca gctctgggac atgtcgcgtc      720
cgcgcacaga cgaagcactc aacgaactcc ttggcatcac caccatccgc gtgacggtct      780
gcgagggcaa aaacctgctt cagcgcgcca acgagttggt gaatccagac gtggtgcagg      840
acgtcgacgc ggccacggcg actcgagggc gttctgcggc gtcgcgcccc accgagcgac      900
ctcgagcccc agcccgctcc gcttctcgcc ccagacggcc cgtcgagtga              950
```

<210> SEQ ID NO 2
<211> LENGTH: 301
<212> TYPE: PRT
<213> ORGANISM: HERPESVIRUS TYPE 1

<400> SEQUENCE: 2

```
Met Thr Ser Arg Arg Ser Val Lys Cys Gly Pro Arg Glu Val Pro Arg
 1               5                  10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Ala Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270
```

```
Thr Arg Gly Arg Ser Ala Ala Ser Arg Pro Thr Glu Arg Pro Arg Ala
        275                 280                 285

Pro Ala Arg Ser Ala Ser Arg Pro Arg Arg Pro Val Glu
        290                 295                 300

<210> SEQ ID NO 3
<211> LENGTH: 144
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 3

Met Gly Ser Ser His His His His His His Ser Ser Gly Leu Val Pro
 1               5                   10                  15

Arg Gly Ser His Met Ala Ser Thr Ala Pro Thr Arg Ser Lys Thr Pro
            20                  25                  30

Ala Gln Gly Leu Ala Arg Lys Leu His Phe Ser Thr Ala Pro Pro Asn
        35                  40                  45

Pro Asp Ala Pro Trp Thr Pro Arg Val Ala Gly Phe Asn Lys Arg Val
    50                  55                  60

Phe Cys Ala Ala Val Gly Arg Leu Ala Ala Met His Ala Arg Met Ala
65                  70                  75                  80

Ala Val Gln Leu Trp Asp Met Ser Arg Pro Arg Thr Asp Glu Asp Leu
                85                  90                  95

Asn Glu Leu Leu Gly Ile Thr Thr Ile Arg Val Thr Val Cys Glu Gly
            100                 105                 110

Lys Asn Leu Leu Gln Arg Ala Asn Glu Leu Val Asn Pro Asp Val Val
        115                 120                 125

Gln Asp Val Pro Asp Pro Glu Arg Lys Thr Pro Arg Val Thr Gly Gly
    130                 135                 140

<210> SEQ ID NO 4
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 4

Gly Ser His Met Ala Arg Thr Ala Pro Thr Arg Ser Lys Thr Pro Ala
 1               5                   10                  15

Gln Gly Leu Ala
            20

<210> SEQ ID NO 5
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 5

Lys Thr Pro Ala Gln Gly Leu Ala Arg Lys Leu His Phe Ser Thr Ala
 1               5                   10                  15

Pro Pro Asn Pro
            20
```

```
<210> SEQ ID NO 6
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 6

Phe Ser Thr Ala Pro Pro Asn Pro Asp Ala Pro Trp Thr Pro Arg Val
 1               5                  10                  15

Ala Gly Phe Asn
            20

<210> SEQ ID NO 7
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 7

Thr Pro Arg Val Ala Gly Phe Asn Lys Arg Val Phe Cys Ala Ala Val
 1               5                  10                  15

Gly Arg Leu Ala
            20

<210> SEQ ID NO 8
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 8

Cys Ala Ala Val Gly Arg Leu Ala Ala Met His Ala Arg Met Ala Ala
 1               5                  10                  15

Val Gln Leu Trp
            20

<210> SEQ ID NO 9
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 9

Arg Met Ala Ala Val Gln Leu Trp Asp Met Ser Arg Pro Arg Thr Asp
 1               5                  10                  15

Glu Asp Leu Asn
            20

<210> SEQ ID NO 10
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 10
```

```
Pro Arg Thr Asp Glu Asp Leu Asn Glu Leu Leu Gly Ile Thr Thr Ile
 1               5                  10                  15

Arg Val Thr Val
            20

<210> SEQ ID NO 11
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 11

Ile Thr Thr Ile Arg Val Thr Val Cys Glu Gly Lys Asn Leu Leu Gln
 1               5                  10                  15

Arg Ala Asn Glu
            20

<210> SEQ ID NO 12
<211> LENGTH: 20
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 12

Asn Leu Leu Gln Arg Ala Asn Glu Leu Val Asn Pro Asp Val Val Gln
 1               5                  10                  15

Asp Val Pro Asp
            20

<210> SEQ ID NO 13
<211> LENGTH: 19
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 13

Asp Val Val Gln Asp Val Pro Asp Pro Glu Arg Lys Thr Pro Arg Val
 1               5                  10                  15

Thr Gly Gly

<210> SEQ ID NO 14
<211> LENGTH: 32
<212> TYPE: PRT
<213> ORGANISM: Artificial Sequence
<220> FEATURE:
<223> OTHER INFORMATION: SYNTHETIC PEPTIDES DERIVED FROM THE VP22TRUNC
      SEQUENCE

<400> SEQUENCE: 14

Thr Pro Arg Val Ala Gly Phe Asn Lys Arg Val Phe Cys Ala Ala Val
 1               5                  10                  15

Gly Arg Leu Ala Ala Met His Ala Arg Met Ala Ala Val Gln Leu Trp
            20                  25                  30
```